United States Patent
Fong et al.

(10) Patent No.: US 10,322,254 B2
(45) Date of Patent: Jun. 18, 2019

(54) SWIVEL ELBOW AND CONNECTOR ASSEMBLY FOR PATIENT INTERFACE SYSTEMS

(75) Inventors: Teck Fong, Bella Vista (AU); Stephen Gray, Sydney (AU); Adam Francis Barlow, Sydney (AU); Robert Thomas Burnham, Sydney (AU); Christopher Scott Skipper, Sydney (AU); David Anthony Pidcock, Sydney (AU); Tumul Gupta, Sydney (AU); Damien Julian Mazzone, Sydney (AU); Jose Ignacio Romagnoli, Sydney (AU); Christopher Samuel Cullen, Sydney (AU)

(73) Assignee: ResMed Limited, Bella Vista (AU)

( * ) Notice: Subject to any disclaimer, the term of this patent is extended or adjusted under 35 U.S.C. 154(b) by 1096 days.

(21) Appl. No.: 14/131,507

(22) PCT Filed: Jul. 6, 2012

(86) PCT No.: PCT/AU2012/000819
§ 371 (c)(1),
(2), (4) Date: Jan. 8, 2014

(87) PCT Pub. No.: WO2013/006899
PCT Pub. Date: Jan. 17, 2013

(65) Prior Publication Data
US 2014/0150798 A1 Jun. 5, 2014

Related U.S. Application Data

(60) Provisional application No. 61/505,711, filed on Jul. 8, 2011, provisional application No. 61/521,139, filed
(Continued)

(51) Int. Cl.
*A61M 16/08* (2006.01)
*A61M 16/20* (2006.01)
*A61M 16/06* (2006.01)

(52) U.S. Cl.
CPC .... *A61M 16/0816* (2013.01); *A61M 16/0616* (2014.02); *A61M 16/0622* (2014.02);
(Continued)

(58) Field of Classification Search
CPC .............. A61M 16/06; A61M 16/0683; A61M 16/0816; A61M 16/0875; A61M 16/0666;
(Continued)

(56) References Cited

U.S. PATENT DOCUMENTS

| 4,621,632 A | 11/1986 | Bartels et al. |
| 4,682,010 A | 7/1987 | Drapeau et al. |

(Continued)

FOREIGN PATENT DOCUMENTS

| CN | 2157298 | 2/1994 |
| CN | 1784250 A | 6/2006 |

(Continued)

OTHER PUBLICATIONS

Communication dated Nov. 19, 2014 issued in European Application No. 12810797.6 (8 pages).
(Continued)

*Primary Examiner* — Jan Christopher L Merene
*Assistant Examiner* — Elliot S Ruddie
(74) *Attorney, Agent, or Firm* — Nixon & Vanderhye P.C.

(57) ABSTRACT

A swivel elbow and connector assembly for a patient interface system includes a ring configured to be sealingly secured in an aperture of the patient interface system. The ring includes a first side in an interior of the patient interface system and a second side at an exterior of the patient interface system when the ring is secured in the aperture.
(Continued)

The ring also includes a plurality of vents configured to permit flow of gases from the interior to the exterior of the patient interface system. The swivel elbow and connector assembly includes an elbow swivelably secured in the ring. A patient interface system for delivering a flow of breathable gas to a user includes a patient interface structure configured to sealing engage the face of the user. The patient interface structure includes an aperture. A swivel elbow and connector assembly is sealingly secured in the aperture.

41 Claims, 39 Drawing Sheets

Related U.S. Application Data on Aug. 8, 2011, provisional application No. 61/648,807, filed on May 18, 2012.

(52) U.S. Cl.
CPC ...... *A61M 16/0825* (2014.02); *A61M 16/208* (2013.01); *A61M 16/0605* (2014.02); *A61M 16/0683* (2013.01); *A61M 2202/0225* (2013.01); *A61M 2205/42* (2013.01); *A61M 2207/00* (2013.01); *A61M 2210/0618* (2013.01)

(58) Field of Classification Search
CPC .............. A61M 16/08; A61M 16/0825; A61M 2210/0618; A61M 16/1075; A61M 16/1085; A61M 16/1095; A61M 16/16; A61M 2205/42; A61M 16/0057; A61M 16/0066; A61M 16/0488; A61M 16/0611; A61M 2207/00; A61M 16/20; A61M 16/201; A61M 16/208; A61M 16/209; F16L 27/04; F16L 37/008; F16L 3/13; F16L 33/22; F16L 33/221; F16L 33/222; A62B 9/00; Y10T 403/7016; Y10T 403/5713; Y10T 403/5761; Y10T 403/5786
USPC ............ 128/205.25, 206.24, 203.27, 206.21, 128/206.26, 207.11, 207.13, 207.18, 128/202.27, 203.17, 204.17, 204.18, 128/204.24, 206.29; 285/148.3, 181, 223, 285/260, 321
See application file for complete search history.

(56) References Cited

U.S. PATENT DOCUMENTS

| | | | |
|---|---|---|---|
| 4,864,684 | A | 9/1989 | Gellenthin, Jr. |
| 5,921,239 | A | 7/1999 | McCall et al. |
| 6,892,729 | B2* | 5/2005 | Smith .................. A61M 16/06 128/202.27 |
| 2003/0196658 | A1* | 10/2003 | Ging ..................... A61M 16/06 128/201.22 |
| 2005/0076912 | A1 | 4/2005 | Eifler et al. |
| 2005/0150497 | A1 | 7/2005 | Eifler et al. |
| 2006/0076017 | A1* | 4/2006 | Walker .................. A61M 16/06 128/205.24 |
| 2006/0201514 | A1 | 9/2006 | Jones et al. |
| 2007/0113852 | A1 | 5/2007 | Martin |
| 2007/0209663 | A1 | 9/2007 | Marque et al. |
| 2008/0168991 | A1 | 7/2008 | Eifler et al. |
| 2008/0210241 | A1 | 9/2008 | Schulz et al. |
| 2009/0044808 | A1 | 2/2009 | Guney et al. |
| 2009/0078259 | A1 | 3/2009 | Kooij et al. |
| 2009/0145429 | A1 | 6/2009 | Ging et al. |
| 2010/0000534 | A1 | 1/2010 | Kooij et al. |
| 2010/0229866 | A1 | 9/2010 | Sullivan |
| 2010/0258133 | A1* | 10/2010 | Todd ................... A61M 15/009 128/207.12 |
| 2010/0307502 | A1 | 12/2010 | Rummery et al. |
| 2010/0319700 | A1* | 12/2010 | Ng ........................ A61M 16/06 128/206.28 |
| 2011/0232649 | A1 | 9/2011 | Collazo et al. |
| 2013/0008439 | A1* | 1/2013 | Selvarajan ............ A61M 16/06 128/202.27 |
| 2013/0199538 | A1* | 8/2013 | Lockhart ........... A61M 16/0816 128/205.25 |

FOREIGN PATENT DOCUMENTS

| | | |
|---|---|---|
| CN | 101228017 A | 7/2008 |
| CN | 101237902 | 8/2008 |
| CN | 101380497 | 3/2009 |
| CN | 101732787 A | 6/2010 |
| CN | 102014999 | 4/2011 |
| CN | 102015000 A | 4/2011 |
| DE | 297 23 101 U1 | 5/1998 |
| GB | 2323418 | 9/1998 |
| JP | 2007-508917 A | 4/2007 |
| WO | WO 97/20597 | 6/1997 |
| WO | 2005/051468 | 6/2005 |
| WO | 2006/024288 A2 | 3/2006 |
| WO | WO 2007/045008 | 4/2007 |
| WO | WO 2009/052560 | 4/2009 |
| WO | WO 2010/139014 | 12/2010 |
| WO | WO 2011/059346 A1 | 5/2011 |
| WO | WO 2012/017213 | 2/2012 |
| WO | WO 2012/030721 | 3/2012 |
| WO | 2013/006899 | 1/2013 |

OTHER PUBLICATIONS

Patent Examination Report No. 1 dated Jul. 14, 2014 issued in Australian Application No. 2012283744 (3 pages).
First Examination Report dated Jul. 24, 2014 issued in New Zealand Application No. 619618 (2 pages).
Third Patent Examination Report dated Apr. 20, 2015 issued in Australian Application No. 2012283744 (3 pages).
Notification of First Office Action dated Jul. 17, 2015 issued Chinese Application No. 201280043012.1 with English translation (17 pages).
First Examination Report dated Aug. 20, 2015 issued in New Zealand Application No. 710684 (2 pages).
Notification of the Second Office Action dated Mar. 29, 2016 issued in Chinese Application No. 201632401615440 with English translation (15 pages).
Office Action dated May 9, 2016 issued in Japanese Application No. 2014-517343 with English translation (6 pages).
Patent Examination Report No. 1 dated Jul. 4, 2016 issued in Australian Application No. 2015234317 (3 pages).
New Zealand Further Examination Report dated Apr. 18, 2013 in New Zealand Application No. 608300 (2 pages).
International Search Report dated Oct. 24, 2013 in International Application No. PCT/AU2012/000819 (6 pages).
Second Patent Examination Report dated Jan. 22, 2015 issued in Australian Application No. 2012283744 (5 pages).
Office Action dated Apr. 1, 2017 issued in Chinese Application No. 201280043012.1 with English translation (9 pages).
Office Action dated Mar. 27, 2017 issued in Japanese Application No. 2014-517343 with English translation (5 pages).
Office Action dated Nov. 13, 2017 issued in Japanese Application No. 2014-517343 with English translation (8 pages).
First Examination Report dated Feb. 24, 2017 issued in New Zealand Application No. 728431 (2 pages).
Extended European Search Report dated Jan. 2, 2018 issued in European Application No. 17189406.6 (8 pages).
Notification of Third Office Action dated Oct. 9, 2016 issued in Chinese Application No. 201280043012.1 with English translation (8 pages).

(56) References Cited

OTHER PUBLICATIONS

Second Examination Report dated Jan. 9, 2017 issued in Australian Application No. 2015234317 (2 pages).
Jan. 21, 2019 Notice of Reasons for Rejection issued in Japanese Application No. 2018-077421 (with translation).

* cited by examiner

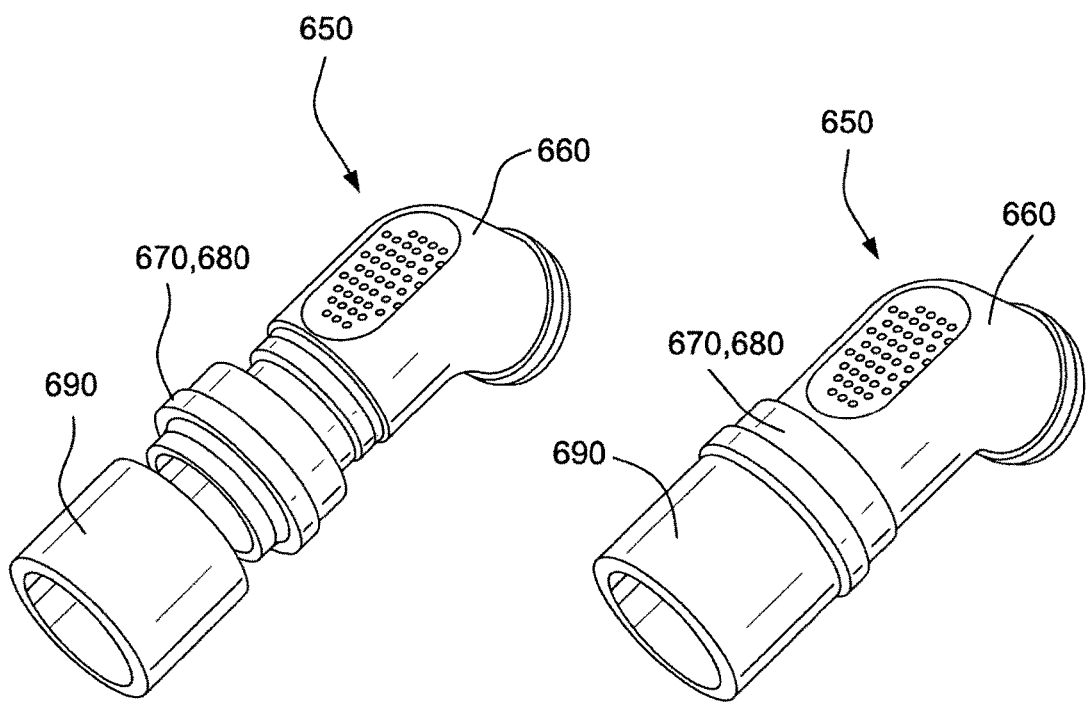
FIG. 61       FIG. 62
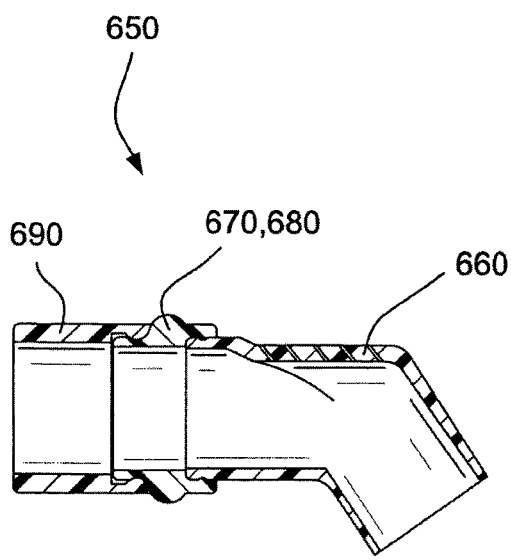
FIG. 63

SWIVEL ELBOW AND CONNECTOR ASSEMBLY FOR PATIENT INTERFACE SYSTEMS

CROSS-REFERENCE TO APPLICATIONS

This application is the U.S. national phase of international Application No. PCT/AU2012/000819 filed 6 Jul. 2012 which designated the U.S and claims priority to U.S. Provisional Applications No. 61/505,711 filed 8 Jul. 2011, U.S. Provisional Application No. 61/521,139 filed 8 Aug. 2011, and U.S. Provisional Application No. 61/648,807 filed 18 May, 2012, the entire contents of which are hereby incorporated by reference.

Further the entire contents of International Application PCT/AU2010/000684, filed Jun. 2, 2010, and published as WO2010/139014A1, are incorporated by reference.

FIELD OF THE TECHNOLOGY

The technology relates to an elbow for a patient interface system, for example a nasal respiratory mask, for an air delivery system for treatment of, for example, Sleep Disordered Breathing (SDB) with Continuous Positive Airway Pressure (CPAP) or Non-Invasive Positive Pressure Ventilation (NIPPV).

BACKGROUND OF THE TECHNOLOGY

Apparatus to deliver breathable gas to a patient typically includes a positive airway pressure (PAP) device, an air delivery conduit or tube, and a patient interface. The patient interface contacts the patient's face in use to deliver pressurized breathable gas to the patient from the PAP device.

SUMMARY OF THE TECHNOLOGY

An aspect of the present technology relates to an elbow and a connector assembly adapted to receive gases from a flow generator and deliver the gases to a patient interface.

An aspect of the present technology relates to an elbow and a connector adapted to vent gases from a patient interface.

As aspect of the present technology is to have multiple functions in one part or component and/or manufactured together, e.g., quick release button(s)/member(s)/actuator(s), baffle and swivel all formed together, so patient is not required to disassemble; this may increase potential for reduced overall part costs.

An aspect of the present technology relates to a multi-axis elbow assembly that allows movement of a connected tube in two separate planes while substantially isolating drag forces from the tube.

Another aspect of the present technology relates to a method for manufacturing an elbow for a patient interface assembly, comprising providing a skeleton, e.g., of rigid or semi-rigid material and adapted to communicate air flow under pressure between an air delivery conduit and a mask; separately molding an anti-asphyxia valve (AAV) with a pull tab; and assembling the skeleton and the AAV by pulling the pull tab from inside the skeleton and through an opening in the skeleton to position, retain and/or seal the AAV relative to the skeleton. The method may include removing at least a portion of the pull tab once pulled through such that an outer flange of the AAV sits flush with an exterior elbow surface. The method may further comprise providing a flexible component to secure the AAV in position. The flexible component may form one or more release buttons or actuators on the elbow.

Another aspect of the present technology relates to an elbow for a patient interface assembly, comprising a skeleton or frame, e.g., of rigid or semi-rigid material, and adapted to communicate air flow under pressure between an air delivery conduit and a mask; an anti-asphyxia valve (AAV) with a pull tab, whereby to assembly the AAV to the skeleton, the pull tab is inserted or guided inside the skeleton and pulled through an opening in the skeleton to position, retain and/or seal the AAV relative to the skeleton. At least a portion of an outer flange of the AAV, once the pull tab is pulled through, sits flush with an exterior elbow surface. The elbow may include a flexible component to secure the AAV in position and/or to form one or more release buttons or actuators on the elbow, the release buttons adapted to remove the elbow from a frame.

Another aspect of the technology relates to a swivel elbow and connector assembly for a patient interface for delivering pressurized breathable gas to a patient from a PAP device. According to one aspect, the swivel elbow and connector assembly is connected to a flexible patient interface structure, e.g. a cushion, through an aperture in the patient interface structure. According to another aspect, the swivel elbow and connector assembly includes a connector, for example a ring, which is attachable to and detachable from the patient interface structure at the aperture. The connector includes a plurality of slots for venting gases from the interior of the patient interface structure to the exterior of the patient interface structure.

Yet another aspect of the technology relates to a swivel elbow connected to the connector and slots to permit venting of gases between the ring and the swivel elbow. According to another aspect, the swivel elbow is connected to the connector and the slots permit venting of gases between the connector and the patient interface structure, e.g. cushion, and no venting occurs between the connector and the swivel elbow.

A further aspect of the technology relates to a swivel elbow and anti-asphyxia valve assembly having a diffuse vent. A still further aspect of the technology relates to a swivel elbow and anti-asphyxia valve assembly having a diffuse vent that may be molded in one piece. An even further aspect of the technology relates to a swivel elbow and anti-asphyxia valve assembly having a diffuse vent that may have engagement portions that, when pressed, permit engagement and disengagement of the swivel elbow and anti-asphyxia valve assembly from a patient interface, e.g. a mask.

According to an example of the technology, a swivel elbow and connector assembly for a patient interface system comprises a ring configured to be sealingly secured in an aperture of the patient interface system, the ring including a first side in an interior of the patient interface system and a second side at an exterior of the patient interface system when the ring is secured in the aperture, the ring comprising a plurality of vents configured to permit flow of gases from the interior to the exterior of the patient interface system; and an elbow swivelably secured in the ring. The ring comprises a first flange on the first side and a second flange on the second side, the first and second flanges defining a channel that sealingly engages the aperture of the patient interface system and the second flange comprises an angled surface that directs the flow of gases from the plurality of vents at an angle to the longitudinal axis of the ring.

According to another example of the technology, a patient interface system for delivering a flow of breathable gas to a user comprises a patient interface structure configured to sealingly engage the face of the user, the patient interface structure comprising an aperture; and a swivel elbow and connector assembly as disclosed herein.

According to another example of the technology, an elbow for delivering gases to a patient interface comprises a first connecting portion, a second connecting portion and a venting portion. The first connecting portion is adapted to receive a tube connection, the second connecting portion is adapted to receive a patient interface assembly, and the venting portion is proximal to the second connecting portion. The venting portion may be diffused about the perimeter of the second connecting portion. The elbow may further comprise a baffle to separate the venting portion from an incoming air stream from the first connecting portion.

According to still another example of the technology, a swivel elbow and anti-asphyxia valve assembly for a patient interface assembly comprises a first component including a first connection portion configured to be sealingly secured in an aperture of the patient interface system, a second connection portion configured to be connected to a swivel or a delivery conduit, one or more first supports between the first connection portion and the second connection portion, and a first aperture and a second aperture are provided between the one or more first supports; and a second component including a valve member, engagement members, and a flexible member, the valve member being between the one or more first supports of the first component and movable between a first position in which the valve member occludes the first aperture and a second position in which the valve member does not occlude the first aperture, the engagement members being configured to engage the one or more first supports when pressed by a user of the patient interface system, and the flexible member being connected to the engagement members and sealing the second aperture.

Other aspects, features, and advantages of the present technology will become apparent from the following detailed description when taken in conjunction with the accompanying drawings, which are a part of this disclosure and which illustrate, by way of example, principles of the technology.

BRIEF DESCRIPTION OF THE DRAWINGS

The accompanying drawings facilitate an understanding of the various examples of this technology. In such drawings:

FIG. 61 is an exploded assembly view of an elbow and tube connector assembly according to another example of the technology;

FIG. 62 is an assembly view of the elbow and tube connector assembly of FIG. 61;

FIG. 63 is a cross sectional view of the elbow and tube connector assembly of FIG. 62;

DETAILED DESCRIPTION OF ILLUSTRATED EXAMPLES

Figure 1:
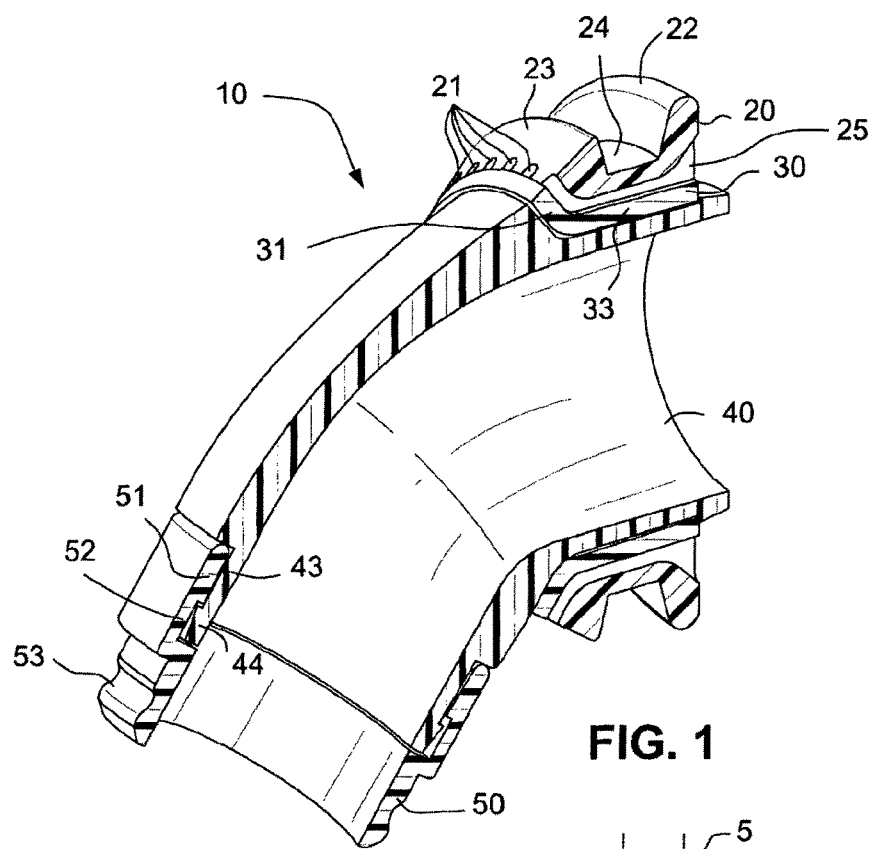
FIG. 1 is an isometric cross sectional view of a swivel elbow and connector assembly according to an example of the technology.

The following description is provided in relation to several examples which may share common characteristics and features. It is to be understood that one or more features of any one example may be combinable with one or more features of the other examples. In addition, any single feature or combination of features in any of the examples may constitute additional examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the PAP devices or blowers described herein may be designed to pump fluids other than air.

The present technology is adapted to provide an arrangement or assembly between a patient interface and a tube that may be adapted to decouple tube drag forces, provide a freedom of movement for the tube to enable a patient to position the tube in a desired position without disrupting the seal, vent exhausted gases and provide a compact, unobtrusive design that is aesthetically acceptable to patients.

The venting arrangement may diffuse the exhausted air to prevent air jetting on patients or their bed partners, and to reduce noise.

The venting arrangement may cooperate with the elbow or connector assembly to further diffuse exhaled air, for example the elbow may be provided with a ridge to deflect air in a diffused manner.

The elbow may be provided with one or more swivel connectors adapted to provide more degrees of movement and aid in decoupling tube drag forces.

The elbow may be referred to as an adaptor, connector or may be described as any element attach an air delivery tube to a patient interface.

Swivel Elbow and Connector Assembly—Vented Connector or Ring

Referring to FIGS. 1-4, a swivel elbow and connector assembly 10 according to an example of the technology comprises a vented elbow connector, or ring, 20 and a swivel elbow 40. A sleeve 30 is provided between the vented elbow ring 20 and the swivel elbow 40. The sleeve 30 is provided between a first end of the swivel elbow 40 and the vented elbow ring 20. A swivel cuff 50 is provided to a second end of the swivel elbow 40 opposite the first end. The swivel cuff 50 comprises a swivel cuff annular engaging ring 51 that is received in an annular groove 43 of the swivel elbow 40 so that the swivel cuff 50 is rotatable, or swivelable, with respect to the swivel elbow 40.

The second end portion of the swivel elbow 40 also includes a tapered flange 44 that is received in an annular groove 52 of the swivel elbow 50 to secure the swivel elbow 50 to the swivel elbow 40. The swivel elbow 40 also includes an end portion 53 that is configured to be connected to an air delivery hose or conduit that is configured to deliver a flow of breathable gas generated by a flow generator, or blower.

Figure 2:
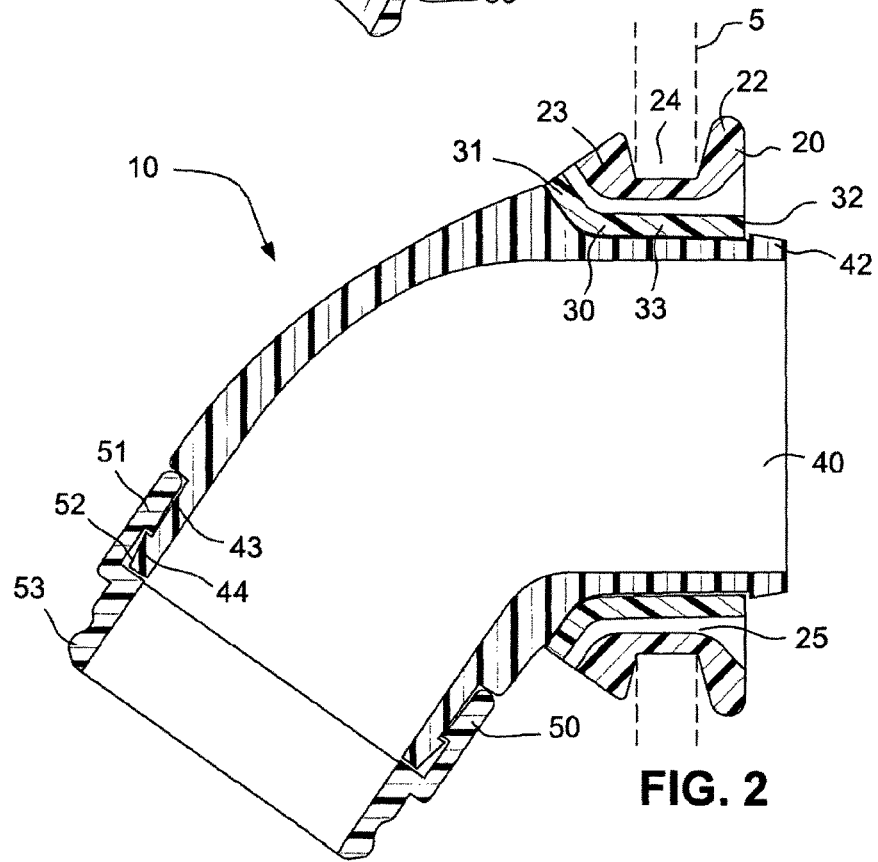
FIG. 2 is a cross sectional side view of the swivel elbow and connector assembly of FIG. 1.
Figure 3:
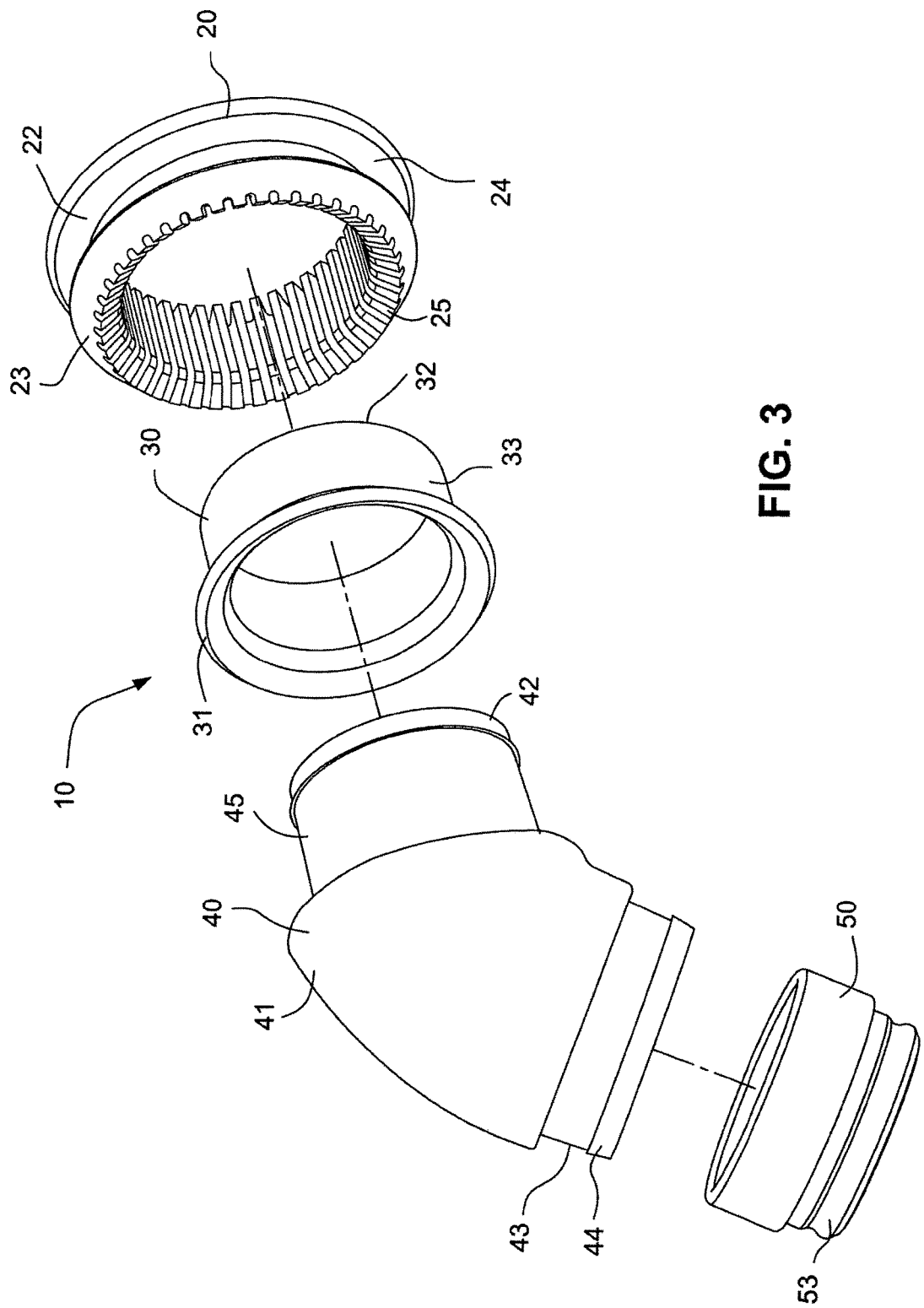
FIGS. 3 and 4 are exploded isometric views of the swivel elbow and connector assembly of FIG. 1.
Figure 4:
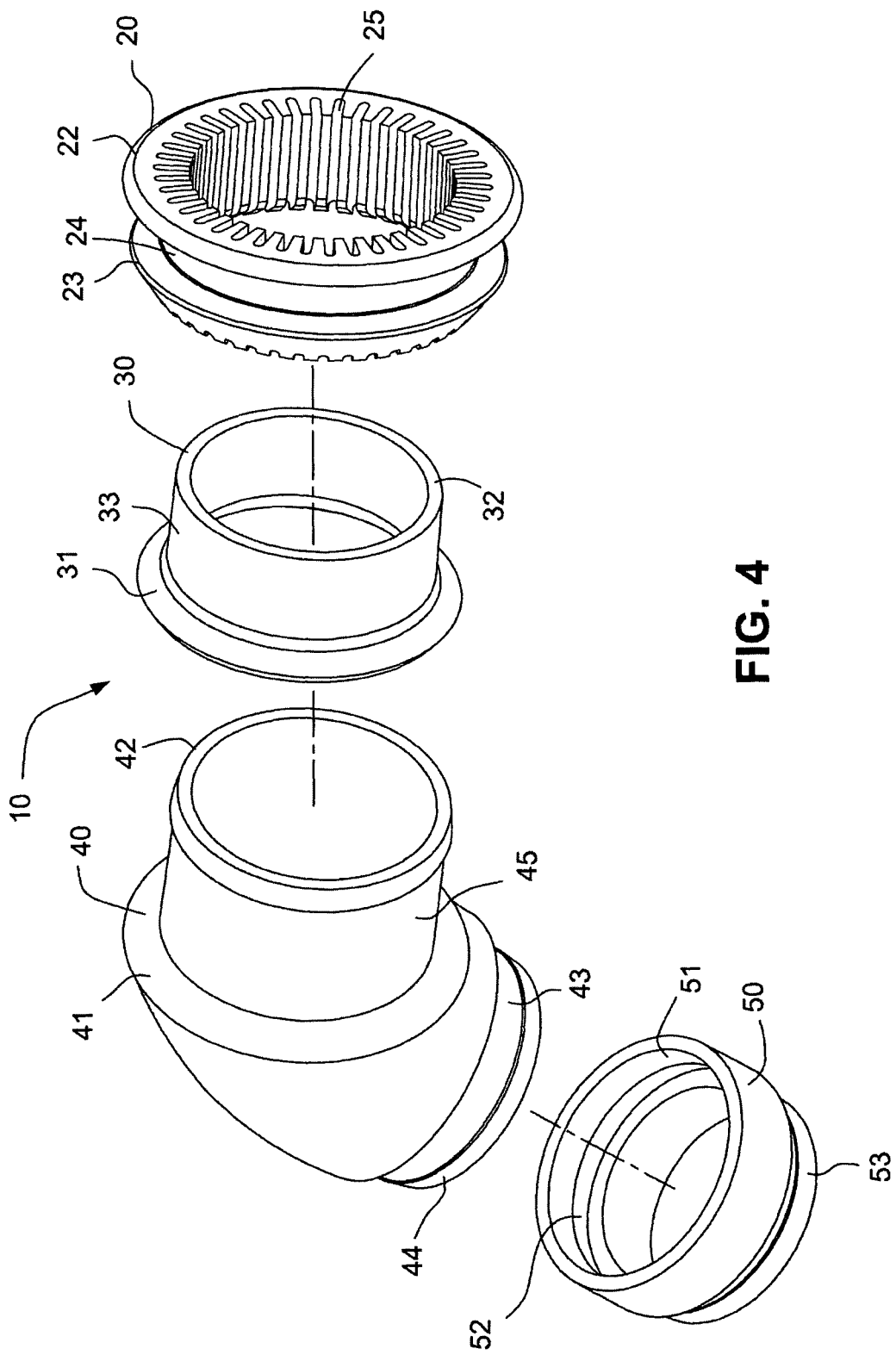

Referring to FIG. 2, the vented elbow ring 20 comprises an inner flange 22 and an outer flange 23. A patient interface structure, e.g. cushion, 5 of a patient interface system may be fitted into a channel 24 of the vented elbow ring 20 defined by the flanges 22, 23. The cushion 5 may be a nasal cushion, a full face cushion, or a nasal pillows or prongs cushion. The patient interface system may also include, for example, a support structure, or frame, that supports the cushion 5; a tube, conduit, or hose configured to deliver a flow of breathable gas to the cushion; and/or a patient interface positioning and stabilizing system (e.g. headgear). It should also be appreciated that the vented elbow ring 20 may be provided in, for example, the support structure or frame.

Figure 31:
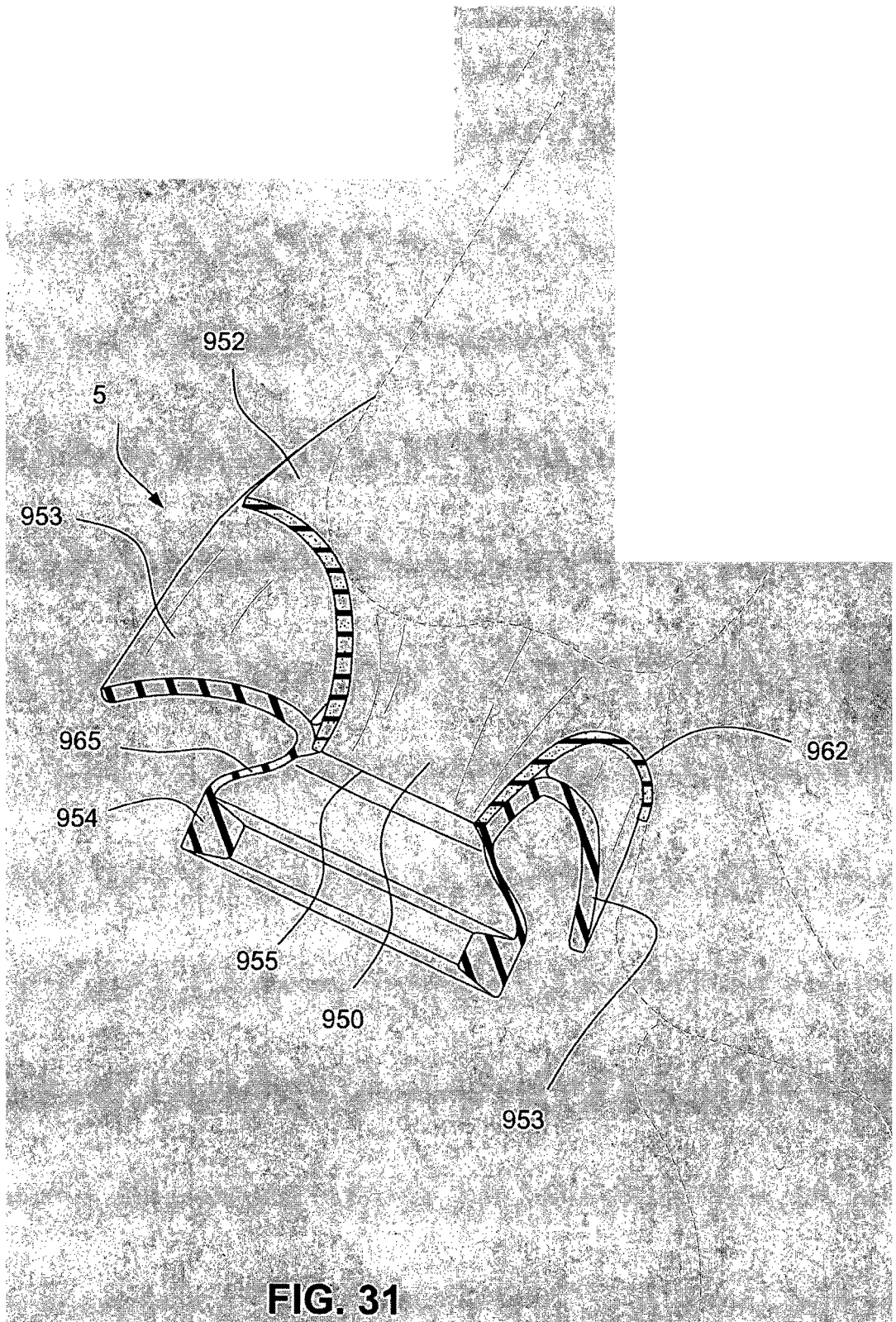
FIG. 31 is a cross sectional view of a patient interface structure, or cushion, usable with examples of the technology.
Figure 32:
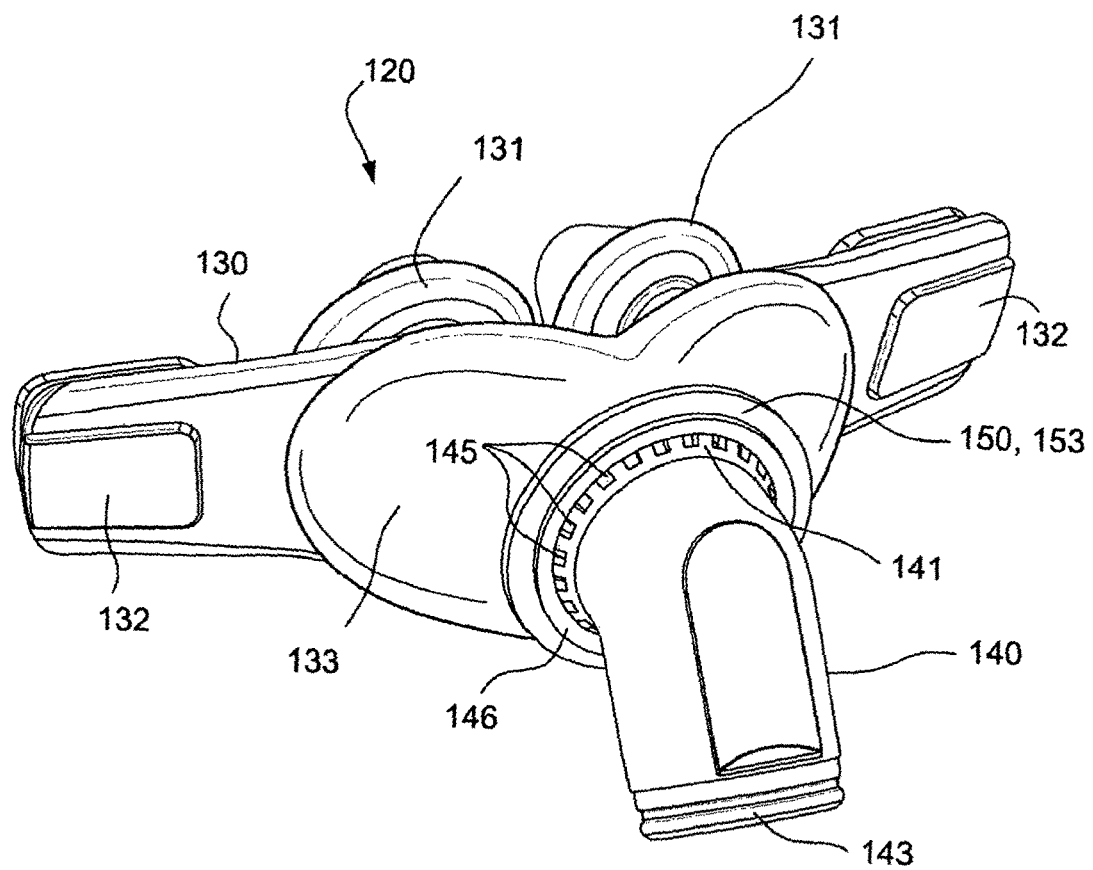
FIG. 32 is an isometric view of a swivel elbow and connector assembly according to an example of the technology.
Figure 33:
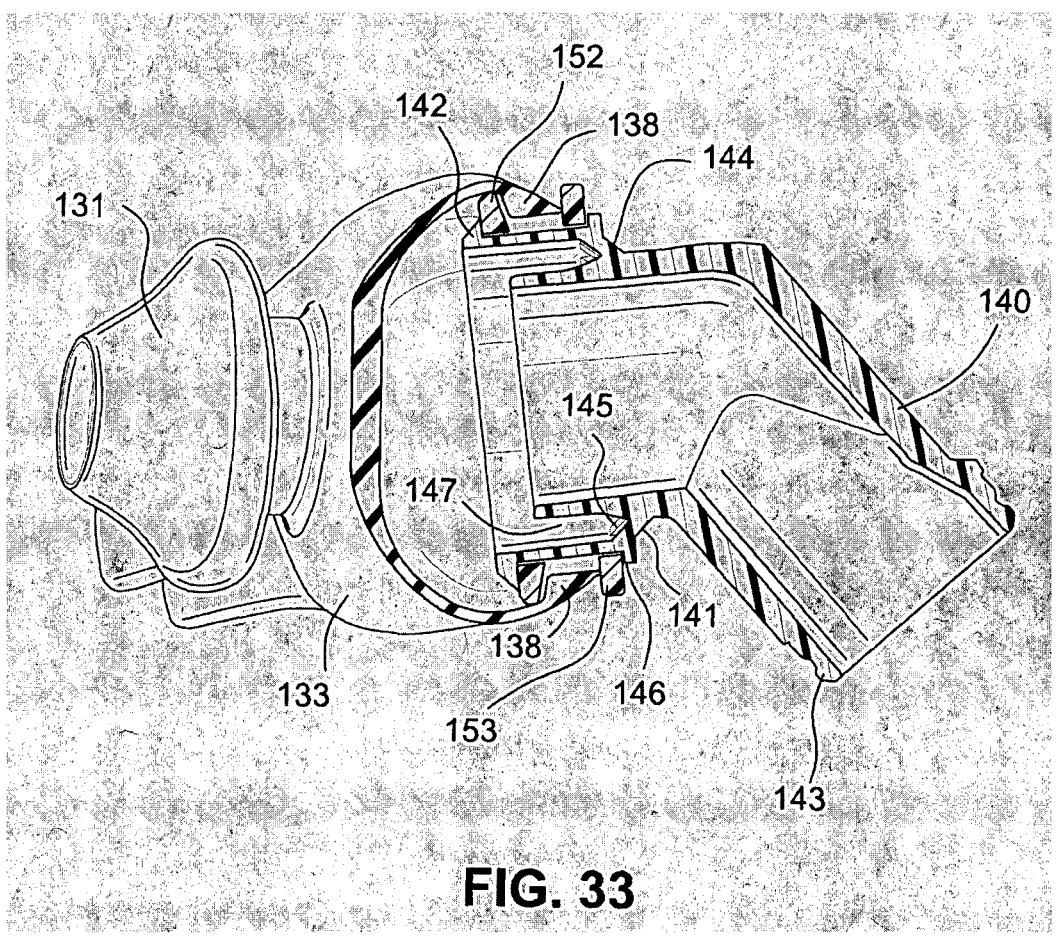
FIG. 33 is a partial side cross sectional view of the swivel elbow and connector assembly of FIG. 32.
Figure 34:
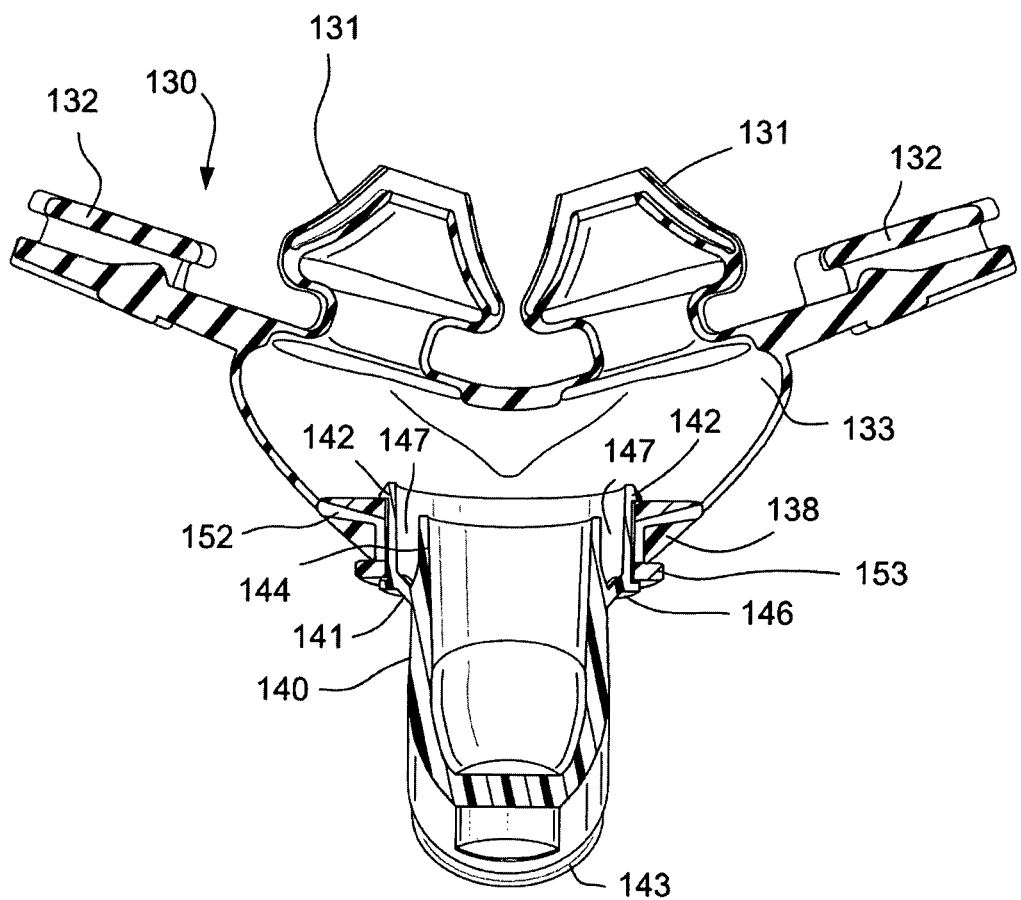
FIG. 34 is a top cross sectional view of the swivel elbow and connector assembly of FIG. 32.

Referring to FIG. 31, a cushion 5 usable with the swivel elbow and connector assembly 10 may include a sealing portion 950 having an upper lip engagement portion 962 that is supported by a supporting portion 953. The sealing portion 950 is separated from the supporting portion 953 by a front gap in an area of a nose tip engagement portion 952. The nose tip engagement portion 952 is flexible and can extend downward when contacted by a patient's nose, but will be limited in how far it can extend if it reaches the supporting portion 953. The nose tip engagement portion 952 is extended in length from the aperture 955 to fit nose tips of different size, so that the nose tip of different patients may engage the nose tip engagement portion at different locations. A stem 954 supports the supporting portion 953 and the sealing portion 950. The cushion 5 may be as disclosed in, for example, International Application PCT/AU2010/00684 (WO 2010/139014 A1), the entire contents of which are incorporated herein by reference. However, it should be appreciated that the swivel elbow and connector assemblies disclosed herein may be used with other patient interface structures or systems, e.g. cushions, such as those disclosed in, for example, U.S. Application 61/443,623 or U.S. 2009/0044808 A1, the entire contents of each being incorporated herein by reference.

The stem 954 may receive the vented elbow ring 20. The vented elbow ring 20 may be inserted into the aperture of the cushion 5 such that the stem 954 is sealingly located in the channel 24 between the flanges 22, 23. The sealing portion 950, the stem 954, and the supporting portion 953 may be a flexible material such as liquid silicone rubber material or another elastomeric material, e.g., TPE, gel or foam. The stem 954 and the supporting portion 953 may be formed together such as in a mold, and the sealing portion 950 may be formed separately and then joined together, e.g. such as by gluing. Alternatively, the stem 954 and the supporting portion 953 may be formed together such as in a mold, and then the sealing portion 950 may be bonded to the supporting portion 953 and the stem 954 in the mold.

The cushion 5 may comprise a flexible gusset 965, which may include the supporting portion 953 and the stem 954. The supporting portion 953 and the stem 954 may be formed as a single unitary element. The flexible gusset 965 may be constructed of a silicone with a hardness of about 20 to 90 Shore A, preferably about 40 Shore A. The flexible gusset 965 could also be made from polycarbonate, polypropylene, nylon, thermoplastic elastomer (TPE), Hytrel™, etc.

Referring again to FIGS. 1-4, the vented elbow ring 20 comprises a plurality of vent slots 25 that extend through the inner flange 22 across the channel 24 and through the outer flange 23. As shown in FIG. 2, the sleeve 30 includes a sleeve flange 31 provided between a flange 41 of the swivel elbow 40 and the flange 23 of the vented elbow ring 20. As shown in FIG. 1, the connection of the sleeve 30 between the swivel elbow 40 and the vented elbow ring 20 provides a plurality of vents 21 for the venting of exhalation gases from the interior of the cushion 5 to the exterior of the cushion 5 through the vent slots 25.

The shape of the vent hole in one example of the present technology may be such that the cross section (e.g., round) is larger on or towards the inside (entry of air) compared to the smaller outside cross sections (e.g., diameter) where the air exits to atmosphere. Also, the exit point or region may be angled to diffuse air away from bed partner/bed clothes, e.g., not perpendicular.

A smooth transition may be provided at the vent passage to help reduce/ensure low noise providing vents along the swivel effectively increase overall length of vents, which may allow for laminar flow development, and result in less noise.

The first end portion of the swivel elbow 40 includes a tapered flange 42 that engages an annular surface 32 of the sleeve 30. A cylindrical portion 33 of the sleeve 30 extends between the sleeve flange 31 and the tapered flange 42 of the swivel elbow 40. The sleeve 30 in the swivel elbow 40 may be permanently assembled by the tapered flange 42 as shown in FIG. 2, although it should be appreciated that the sleeve 30 may be under molded, co molded or otherwise formed with the swivel elbow 40 to reduce assembly costs.

Referring to FIG. 1, the swivel elbow and connector assembly 10 may be provided with a plurality of vents 21, for example, 20-60 vents, for example 30-50 vents, for example 38 vents, 40 vents or 42 vents. The cross sectional area of the vents may vary from, for example, 0.5 mm×0.5 mm, for example, 1.0 mm×1.0 mm, or 0.7 mm×0.7 mm.

The sleeve flange 31 and the flange 41 of the swivel elbow 40 may be provided at an angle that provides for venting of the exhalation gases from the interior of the cushion 5, 360° around the swivel elbow 40 and in direction away from the face of the patient. The sleeve 30 provides good diffusivity, and the vent path is contained and easily adjustable. The formation of the vents 21 by the sleeve 30 also reduces the noise of the venting from the interior of the cushion 5.

Figure 35:
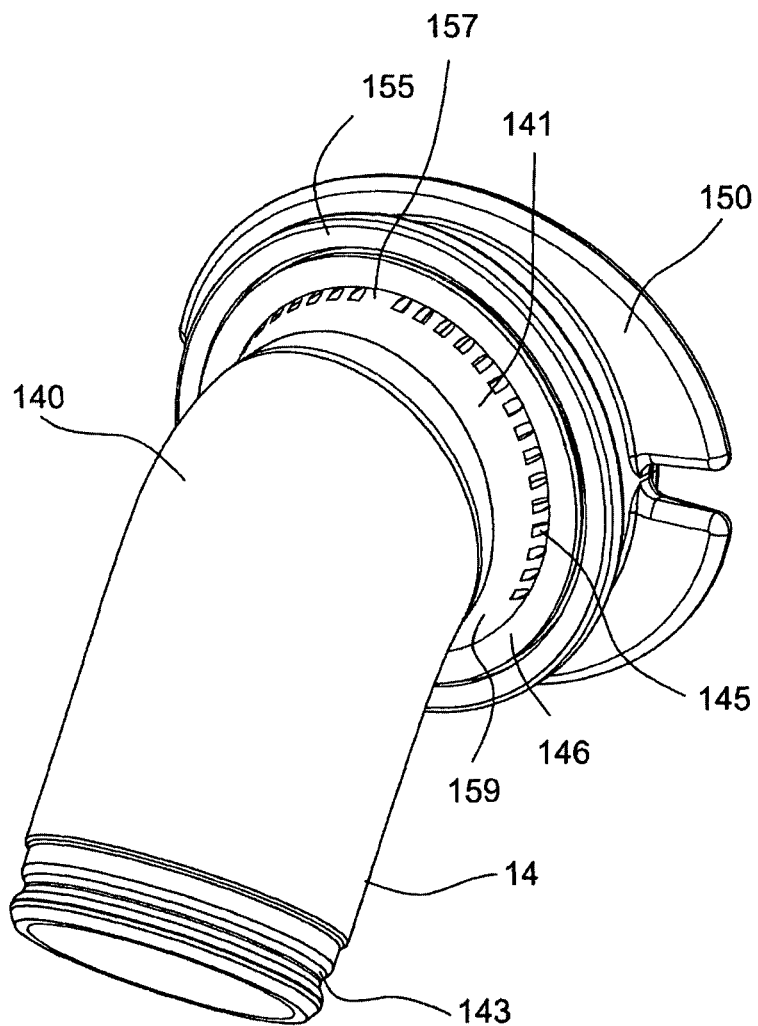
FIG. 35 is an isometric view of a variation of the swivel elbow and connector assembly of FIG. 32.
Figure 36:
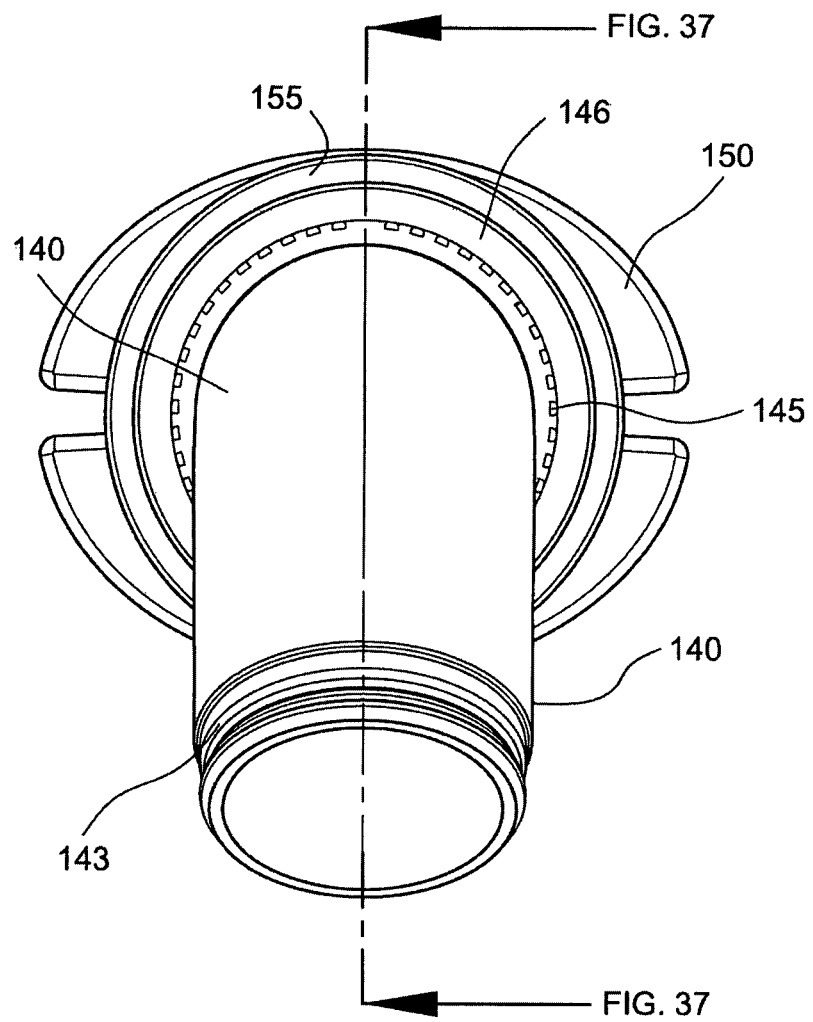
FIG. 36 is a front view of the swivel elbow and connector assembly of FIG. 35.

Although the vented elbow ring 20 is shown in FIGS. 1-4 as circular, it should be appreciated that the vented elbow ring may be, for example, elliptical in cross section, as show in FIGS. 35 and 36.

Swivel Elbow and Connector Assembly—Vented Elbow

Referring to FIGS. 32-37, a swivel elbow and connector assembly 120 according to another example comprises a swivel elbow 140 and a connector, or ring, 150. A cushion 130 comprises a flexible base 133 comprising an aperture for sealingly receiving the ring 150. The flexible base may comprise a flange, or stem, 138 that is configured to be received in a channel 154 of the ring 150 that is defined between an inner flange 152 and an outer flange 153. The cushion 130 may comprise nasal pillows 131 for sealingly engaging the nares of a patient or user and connectors 132 for connecting the cushion 130 to a patient interface structure positioning and stabilizing system (e.g. headgear). The cushion 130 may be as disclosed in, for example, International Application PCT/AU2008/001.557 (WO 2009/052560 A1), the entire contents of which are incorporated herein by reference. It should be appreciated that other cushions or patient interface structures may also be used with the assembly 120, including rigid or semi-rigid patient interface support structures (e.g. frames).

The elbow 140 includes a first end 143 configured for connection to, for example, a delivery hose or conduit. The elbow includes a tapered flange 142 at a second end for securing the elbow 140 to the ring 150. Intermediate the first and second ends, the elbow 140 includes an angled flange 141 having a plurality of vents 145 spaced around the flange 141. The flange 141 is angled with respect to the longitudinal axis of the elbow 140. The number and size of the vents may be as described above. It should also be appreciated that the vents 145 may be distributed around the angled flange 141 evenly or randomly. It should further be appreciated that the vents 145 may not extend around the entire circumference of the angled flange 141 of the elbow 140, for example as shown in FIG. 35.

A radial flange 146 may surround the angled flange 141 that engages the outer flange 153 of the ring 150. The ring 150 is secured between the tapered flange 142 and the radial flange 146. The elbow 140 may further comprise a baffle 144 to separate the venting portion 147 from an incoming flow of breathable gas from the first end 143, although it may be circular or have other shapes as well.

Figure 37:
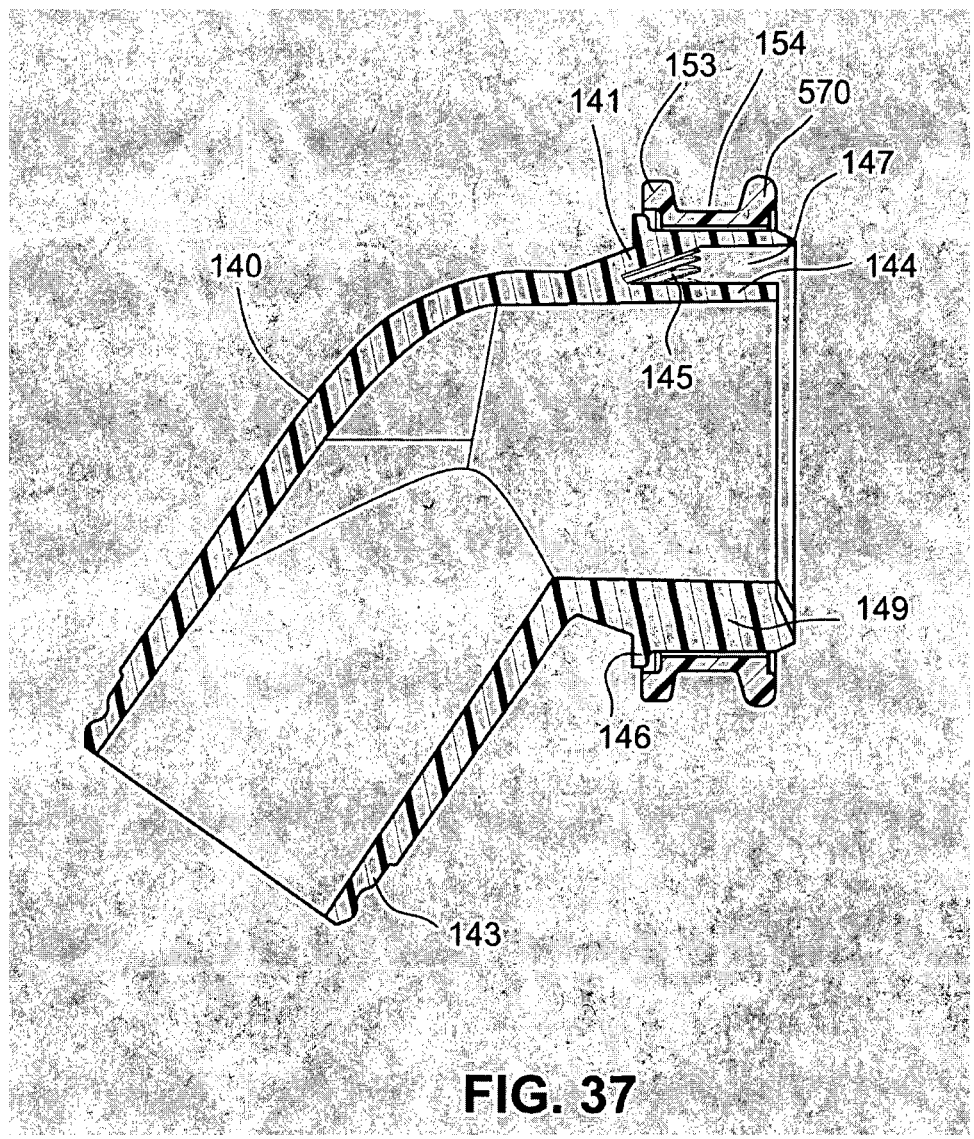
FIG. 37 is a cross sectional view of the swivel elbow and connector assembly of FIG. 35.

Referring to FIGS. 35-37, the ring 150 may have an elliptical configuration (e.g. elliptical cross section). A circular radial flange 155 may be provided on the ring 150 to form a sealing interface with the radial flange 146 of the elbow 140. As also shown in FIG. 35, the vents 145 may not be provided around the entire circumference of the elbow, for example the lower portion 159 of the angled flange 141 may not include vents 145, and/or the angled flange 141 may have a reinforced portion 157 between vents 145. As shown in FIG. 37, the baffle 144 of the elbow 140 also has an elliptical configuration that provides venting portions 147 and non-venting portion 149 to the elbow 140.

Double Swivel Elbow and Connector Assembly—Vented Connector or Ring

Figure 5:
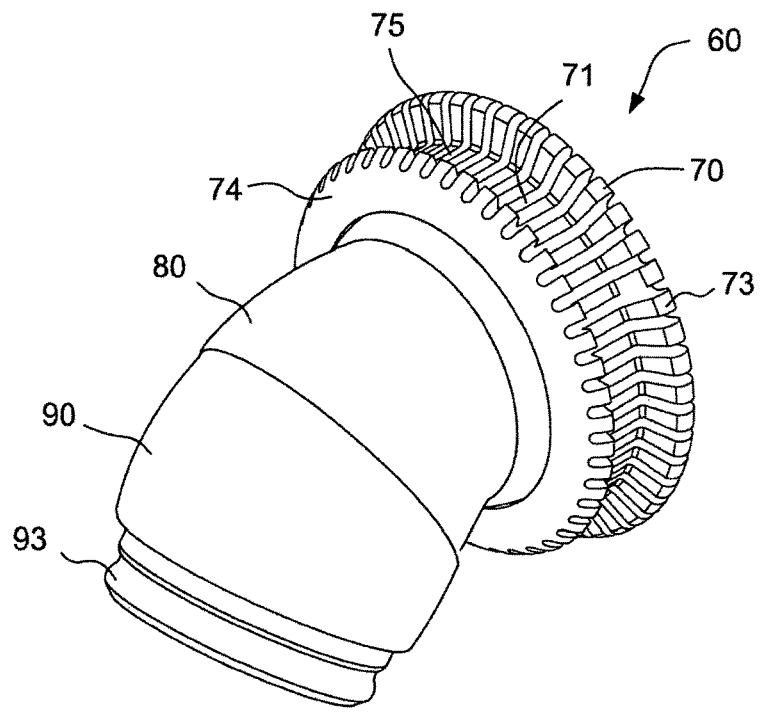
FIGS. 5 and 6 are isometric views of a double swivel elbow and connector assembly according to another example of the technology in a first position or configuration.
Figure 6:
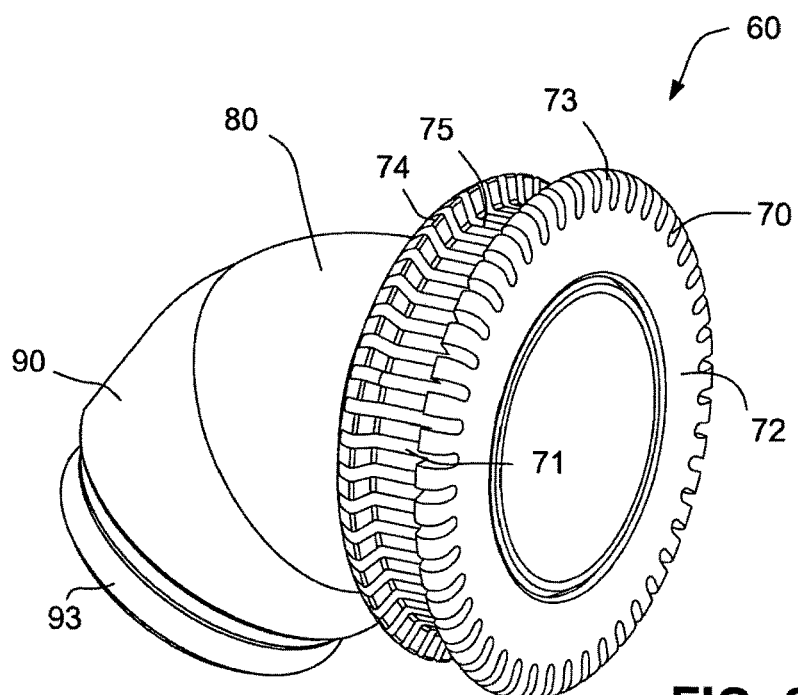
Figure 7:
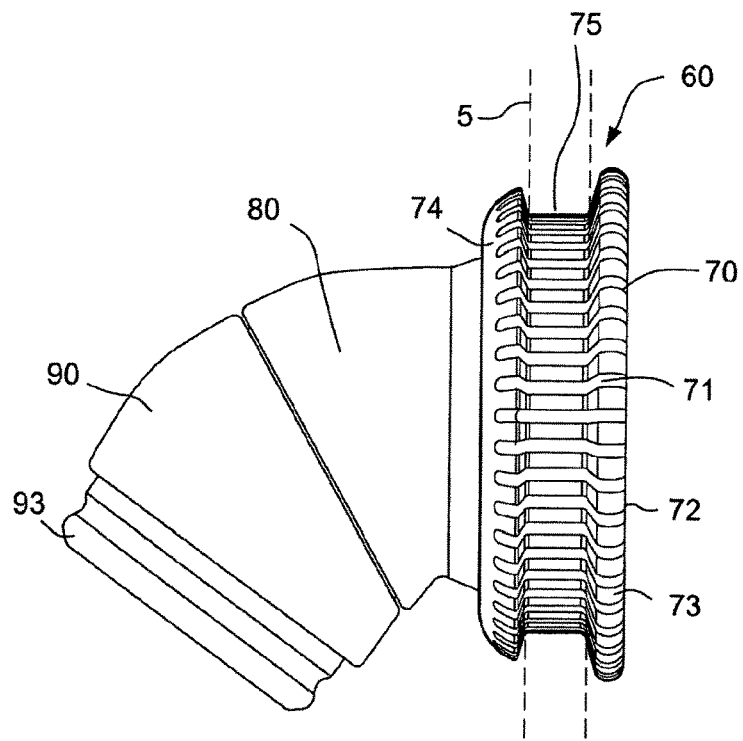
FIG. 7 is a side view of the double swivel elbow and connector assembly of FIGS. 5 and 6.

Referring to FIGS. 5-16, a double swivel elbow and connector assembly 60 according to a example comprises a ball and socket connection i.e. a ball joint vented elbow ring 70, a ball joint swivel elbow 80 swivelably connected to the ball joint vented elbow ring 70, and a swivel cuff 90 swivelably connected to the ball joint swivel elbow 80. The ball joint vented elbow ring 70 includes a plurality of vent slots 71 extending around the periphery of the elbow ring 70. As shown in FIG. 7, the slots 71 extend through an inner flange 73 of the elbow ring 70 and through an outer flange 74 of the elbow ring 70. A cushion 5 having an aperture may be received in a channel 75 between the inner flange 73 and the outer flange 74. When the elbow ring 70 is positioned in the aperture of the cushion 5, vent holes are created between the vent slots 71 in the elbow ring 70 and the cushion 5. The cushion 5 is secured to the double swivel elbow and connector assembly 60 when the stem 454 of the cushion is received in the channel 75 of the vented elbow ring 70. As used herein, the term "sealingly secured" means that the flow of breathable gas delivered to the patient interface system, e.g. cushion, through the swivel elbow will not pass from the interior to the exterior of the patient interface system through the vents in the absence of exhalation by the patient or wearer of the patient interface system.

Figure 10:
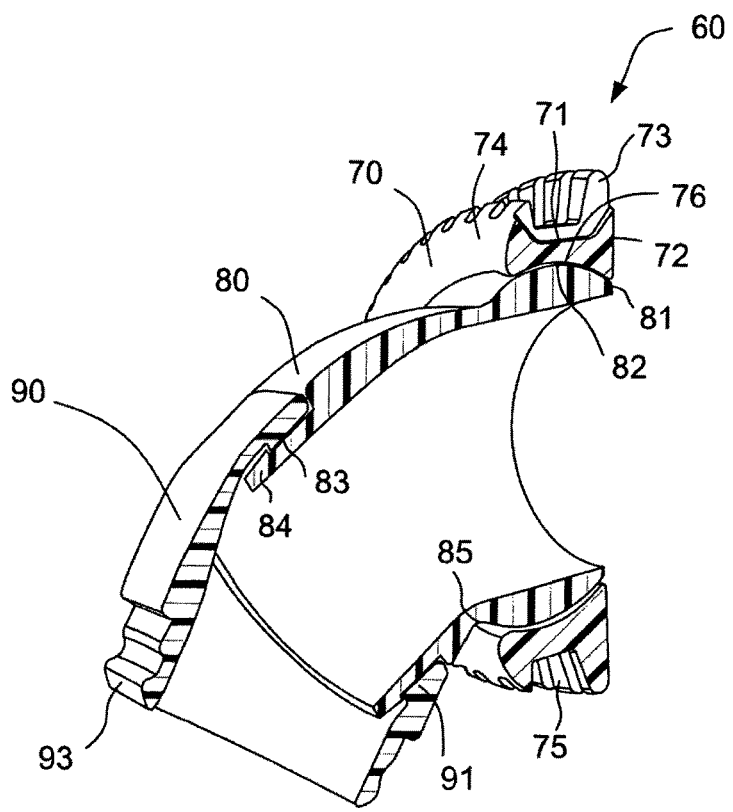
FIG. 10 is an isometric cross sectional view of the double swivel elbow and connector assembly in the first position.
Figure 11:
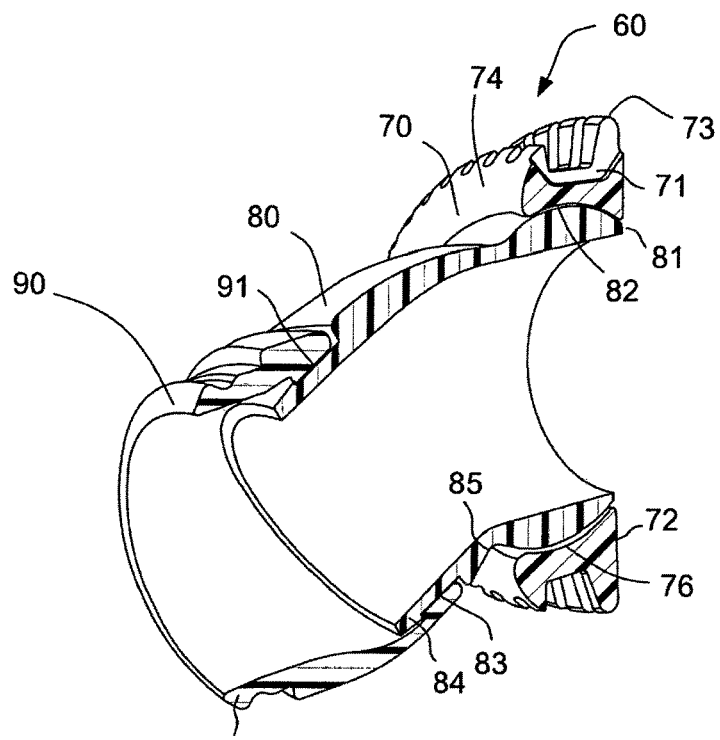
FIG. 11 is an isometric cross sectional view of the double swivel elbow and connector assembly in the second position.

Referring to FIG. 6, the vented elbow ring 70 includes an annular surface 72 that may be flush or in line with an annular surface 81 of the ball joint swivel elbow 80 when the double swivel elbow and connector assembly 60 is in the position or configuration shown in FIGS. 5-7, i.e., with the elbow pointing generally downward. As shown in FIG. 10, the ball joint swivel elbow 80 includes an arcuate annular, or partially spherical, outer surface 82 that is swivelably contained by an arcuate annular, or partially spherical, inner surface 76 of the vented elbow ring 70. The vented elbow ring 70 and the ball joint swivel elbow 80 thus act as a ball joint connection between the vented elbow ring 70 and the swivel elbow 80. The inner surface 76 and the outer surface 82 have radii of curvature that are approximately equal. The substantially equal radii of curvature may be achieved by molding the vented elbow ring 70 and the swivel elbow 80 together, without the vented elbow ring 70 and the swivel elbow 80 chemically bonding or mechanically bonding in the mold, e.g., by shrinkage. The inner surface 76 and the outer surface 82 are engaged essentially over the area of contact between the surfaces so that no or little gas flows between the ring 70 and the elbow 80.

Figure 12:
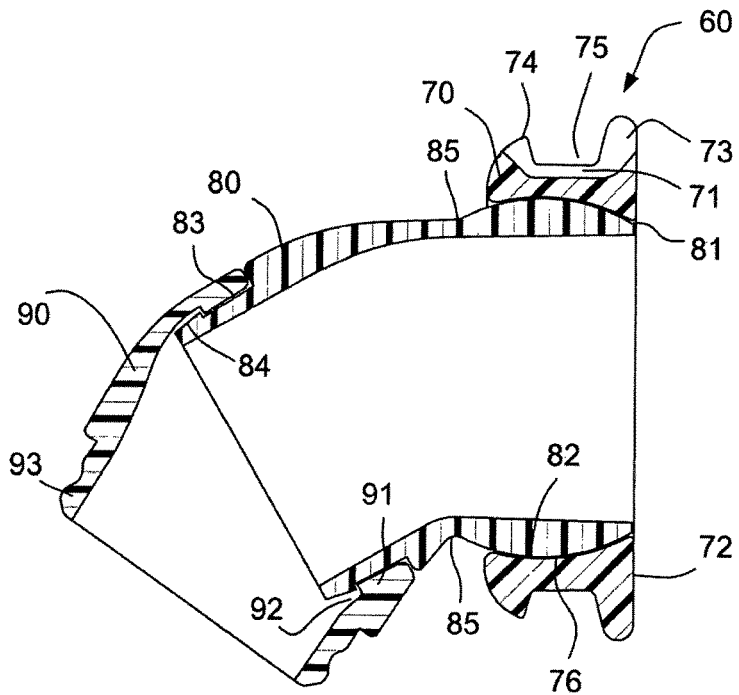
FIG. 12 is a cross sectional side view of the double swivel elbow and connector assembly in the first position.
Figure 13:
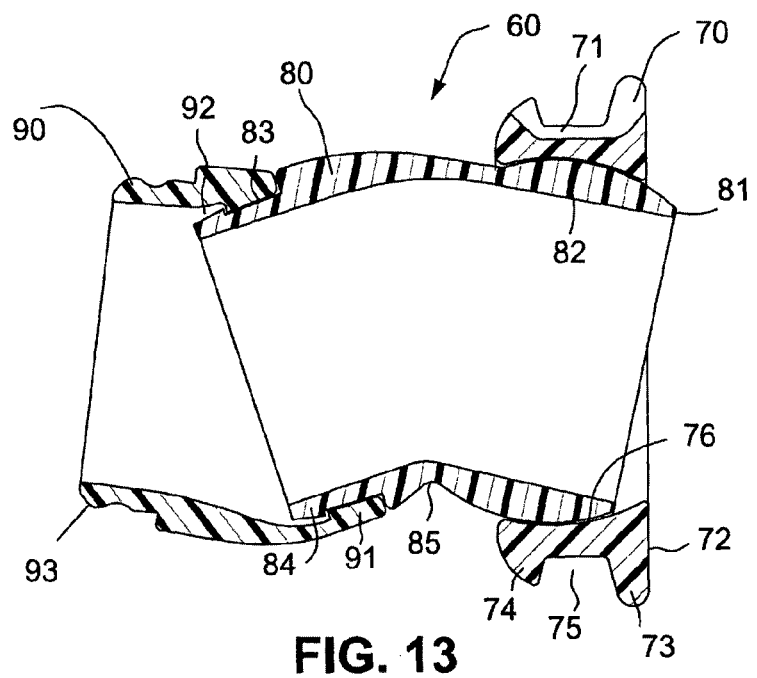
FIG. 13 is a cross sectional side view of the double swivel elbow and connector assembly in a third position or configuration.
Figure 15:
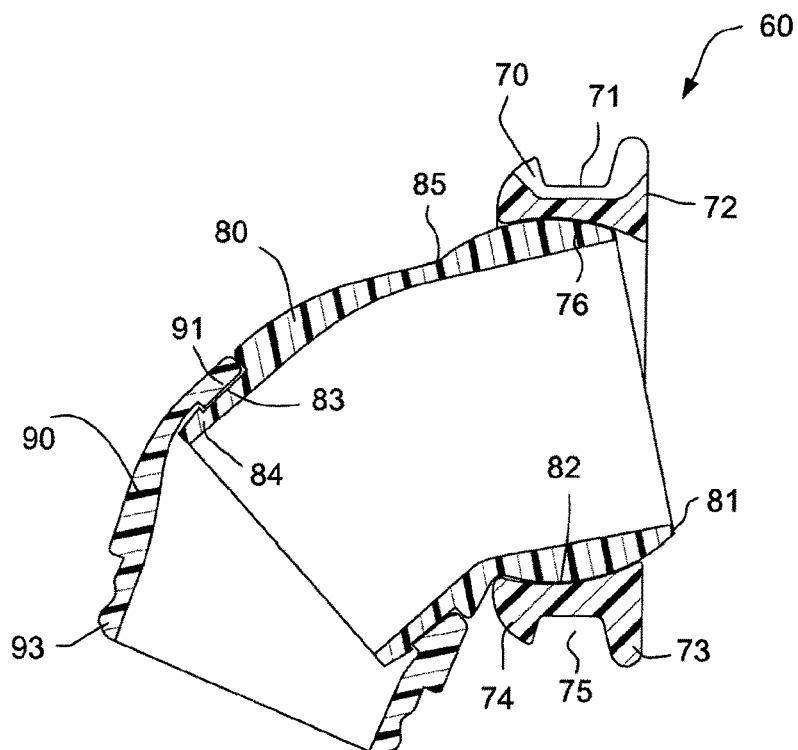
FIG. 15 is a cross sectional side view of the double swivel elbow and connector assembly in a fourth position or configuration.
Figure 16:
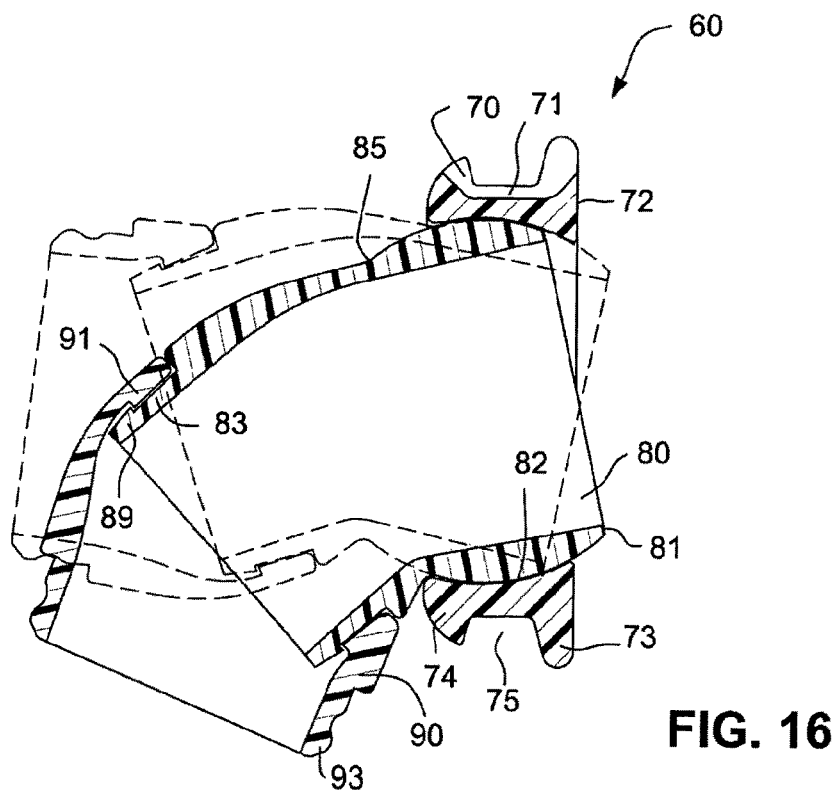
FIG. 16 is a cross sectional side view of the transition of the double swivel elbow and connector assembly from the third position to the fourth position.
Figure 17:
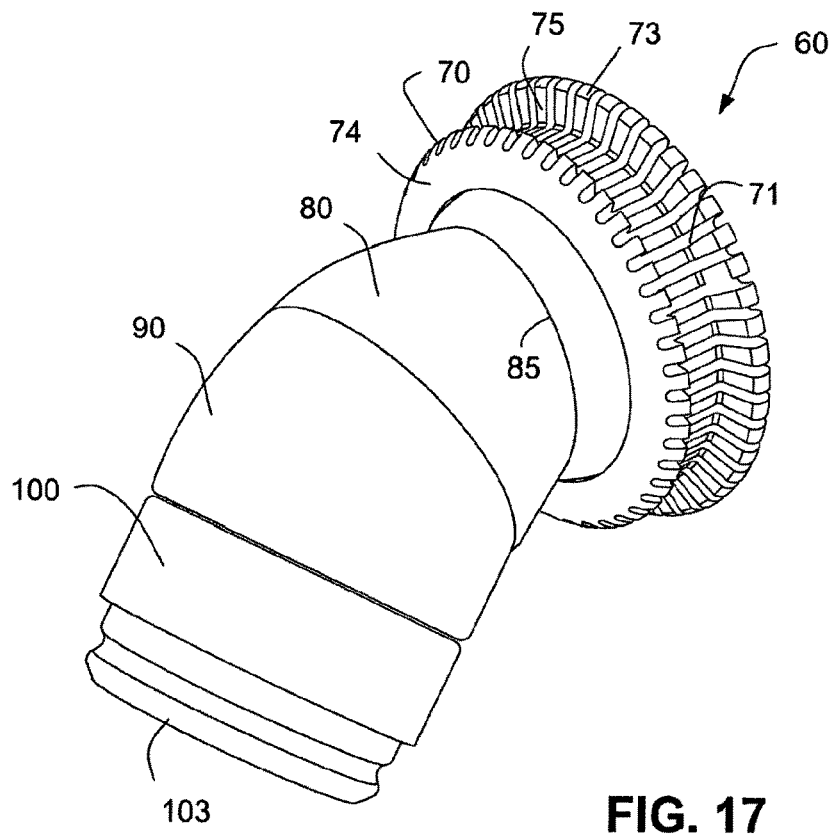
FIGS. 17 and 18 are isometric views of a triple swivel elbow and connector assembly including a second swivel cuff according to still another example of the technology in a first position or configuration.
Figure 18:
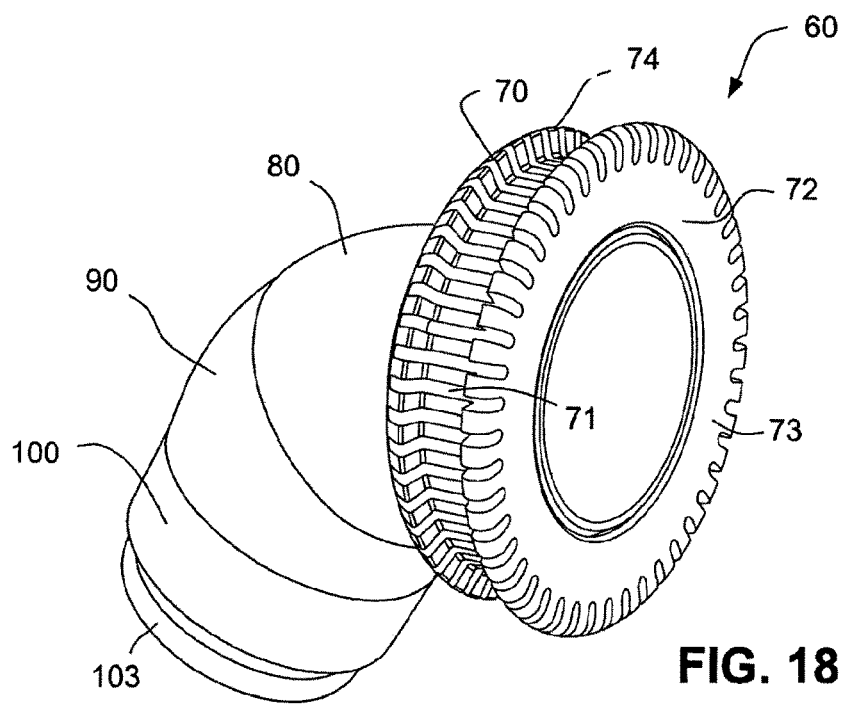
Figure 19:
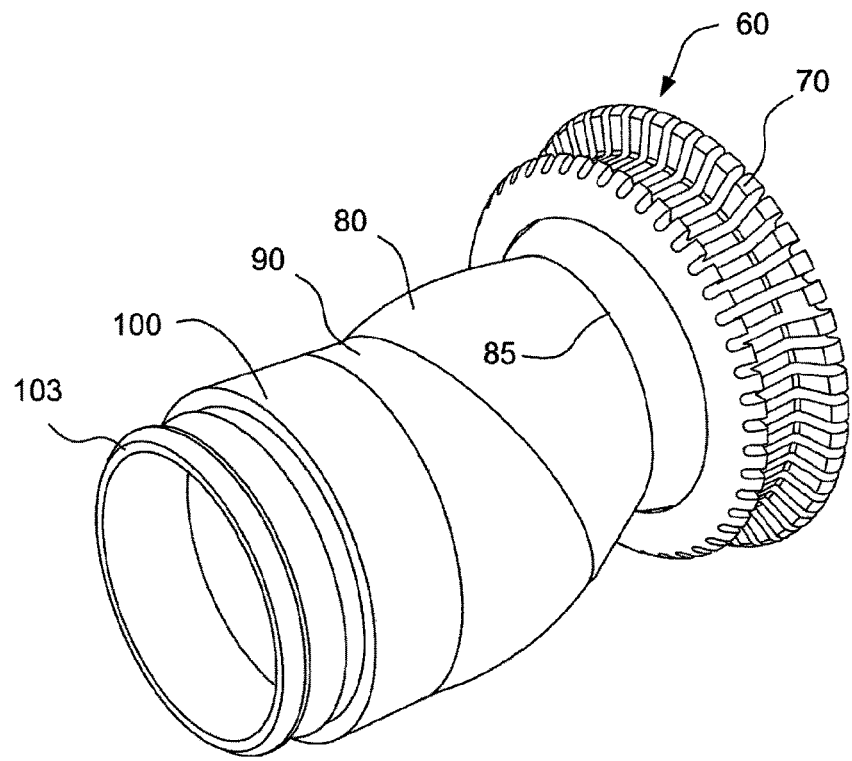
FIG. 19 is an isometric view of the triple swivel elbow and connector assembly of FIGS. 17 and 18 in a second position or configuration.
Figure 20:
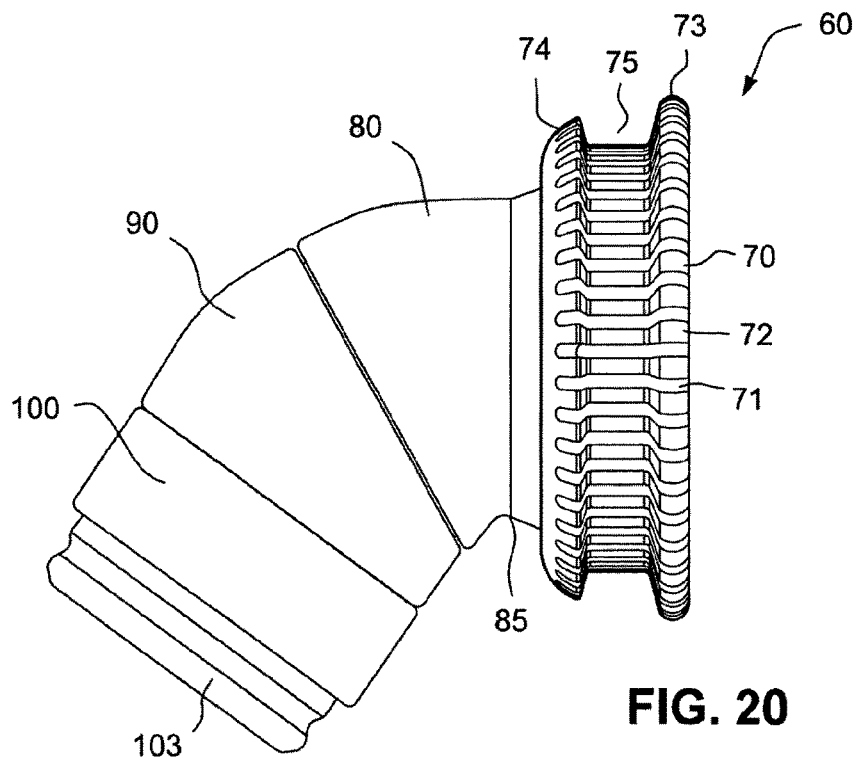
FIG. 20 is a side view of the triple swivel elbow and connector assembly of FIGS. 17 and 18.

The swivel elbow 80 may swivel from the position shown in FIG. 12, in which the annular surface 81 is flush with the annular surface 72 of the vented elbow ring 70 and the longitudinal axes of the ring 70 and the elbow 80 are co-linear, to the position shown in FIGS. 13, 15 and 16, in which the annular surfaces 72, 81 are not flush and the longitudinal axes are at an angle to each other. An annular junction 85 between the arcuate annular outer surface 82 of the swivel elbow 80 and the end portion of the swivel elbow 80 limits the swiveling of the elbow 80 within the vented elbow ring 70, as shown in FIGS. 13, 15 and 16.

Referring to FIGS. 10-16, the end portion of the swivel elbow 80 includes an annular groove 83 that receives a tapered annular engaging ring 91 of the swivel cuff 90. A tapered flange 84 of the swivel elbow 80 engages the tapered annular engaging ring 91 of the swivel cuff 90 to retain the swivel cuff 90 to the swivel elbow 80. As shown in FIGS. 12 and 13, the swivel cuff 90 includes an angled groove 92 that allows the swivel cuff 90 to rotate from the position shown in FIG. 12 to the position shown in FIG. 13.

Figure 9:
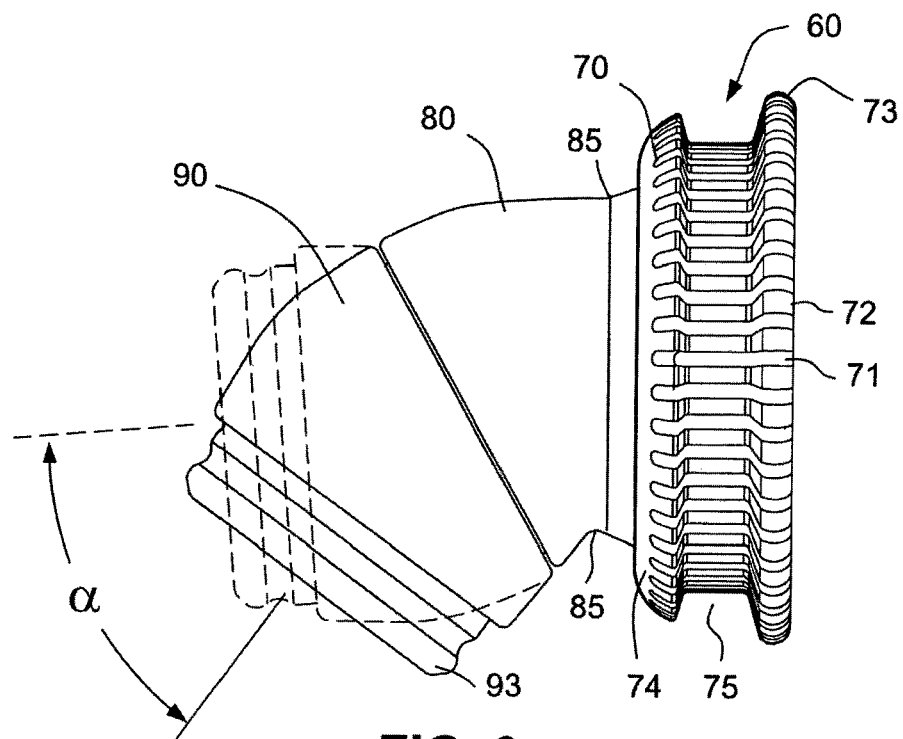
FIG. 9 is a side view of the transition of the double swivel elbow and connector assembly from the first position to the second position.
Figure 14:
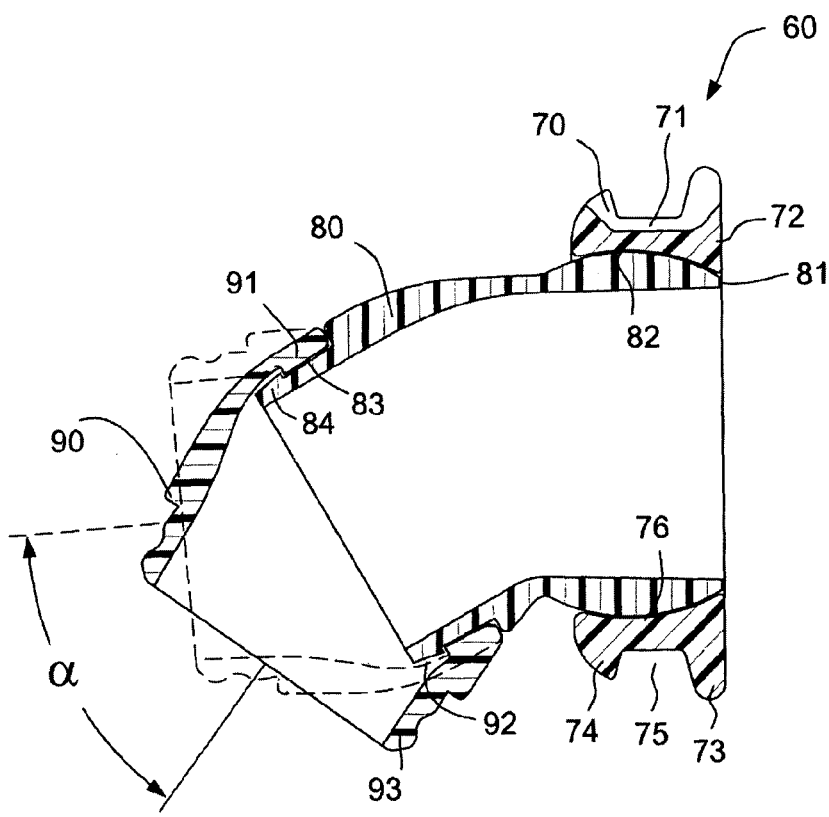
FIG. 14 is a cross sectional side view of the transition of the double swivel elbow and connector assembly from the first position to the second position.

Referring to FIGS. 9 and 14, the pivoting of the swivel cuff 90 allows a longitudinal axis of the double swivel elbow and connector assembly 60 to rotate through an angle α of, for example, 40-60°, for example 50°.

Figure 8:
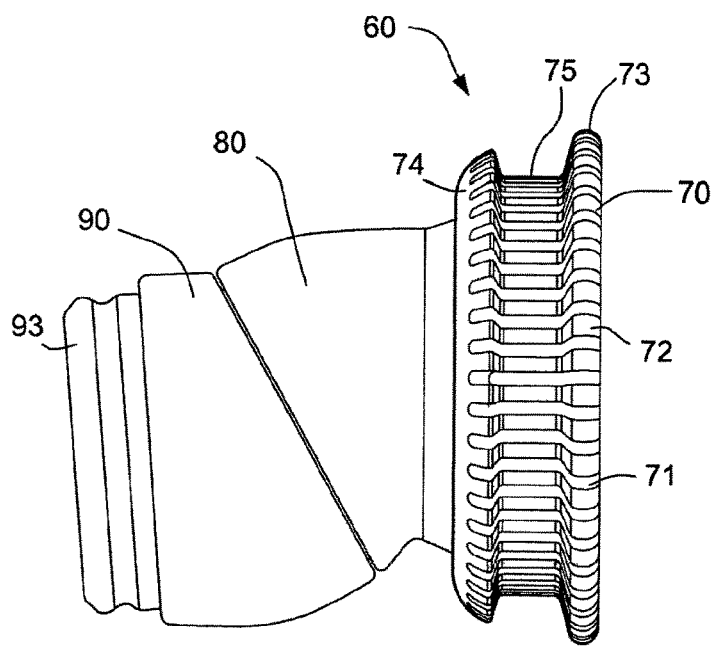
FIG. 8 is a side view of the double swivel elbow and connector assembly of FIG. 7 in a second position or configuration.

The double swivel elbow and connector assembly 60 allows for swiveling of the connection of an air delivery tube or conduit to the swivel cuff end portion 93 in two directions. For example, as shown in FIGS. 7 and 8, the swivel cuff 90 may swivel from the position shown in FIG. 7 to the position shown in FIG. 8 while the swivel elbow 80 remains in a position such that the annular surface 81 of the swivel elbow is flush with the annular surface 72 of the vented elbow ring 70. The transition from the alignment shown in FIG. 7 to the alignment shown in FIG. 8 is shown in FIG. 9 as a central axis of the swivel cuff 90 rotates through the angle α of, for example, 50°. The swiveling of the cuff 90 from the position shown in FIG. 7 to the position shown in FIG. 8 allows a short air delivery tube or conduit to straighten out thereby reducing torque forces applied to the vented elbow ring 70 and cushion 5. In other masks without this swivel, if the tube is pulled in a direction that is perpendicular to the central axis of the elbow, because the elbow has an L shaped configuration and no swivel, it cannot rotate to be in line with the tube; therefore this pulling force is directly applied to the mask and can disrupt the seal. The ball joint (or ball and socket connection) design allows the elbow and the swivel to re-align depending on the forces being exerted by the tube.

The double swivel elbow and connector assembly 60 also permits the swivel elbow 80 to swivel with respect to the vented elbow ring 70, for example, from the position shown in FIG. 13 to the position shown in FIG. 15. The pivoting or swiveling of the swivel elbow 80 is limited by the annular junction 85 between the arcuate annular outer surface 82 of the swivel elbow 80 and the end portion of the swivel elbow 80. The swivel elbow 80 may also swivel from the position shown in FIG. 13 to the position shown in FIG. 16 while the swivel cuff 90 may also pivot or swivel with respect to the swivel elbow 80.

Triple Swivel Elbow and Connector Assembly—Vented Connector or Ring

Referring to FIGS. 17-30, a triple swivel elbow and connector assembly 60 according to another example comprises a second swivel cuff 100 swivelably connected to the end portion of the swivel cuff 90. The second swivel cuff 100 comprises a tapered annular engaging ring 101 that is received in an annular groove 95 in the end portion of the swivel cuff 90. A tapered flange 94 is provided at the end of the swivel cuff 90 to engage and retain the annular engaging ring 101 of the second swivel cuff 100. The second swivel cuff 100 includes an annular groove 102 that receives the tapered flange 94 of the swivel cuff 90. The second swivel cuff 100 includes an end portion 103 that is configured to receive an air delivery tube or conduit for receiving a flow of breathable gas provided by a flow generator, or blower, for delivery into a patient interface including the cushion 5.

Figure 21:
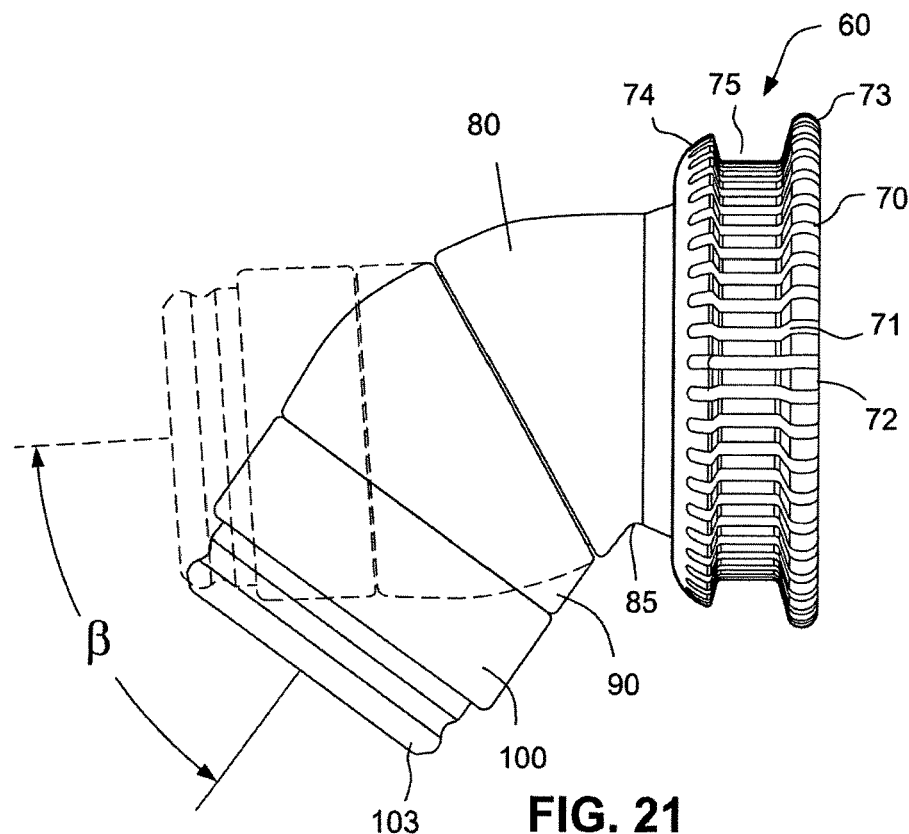
FIG. 21 is a side view of the transition of the triple swivel elbow and connector assembly from the first position to the second position.
Figure 22:
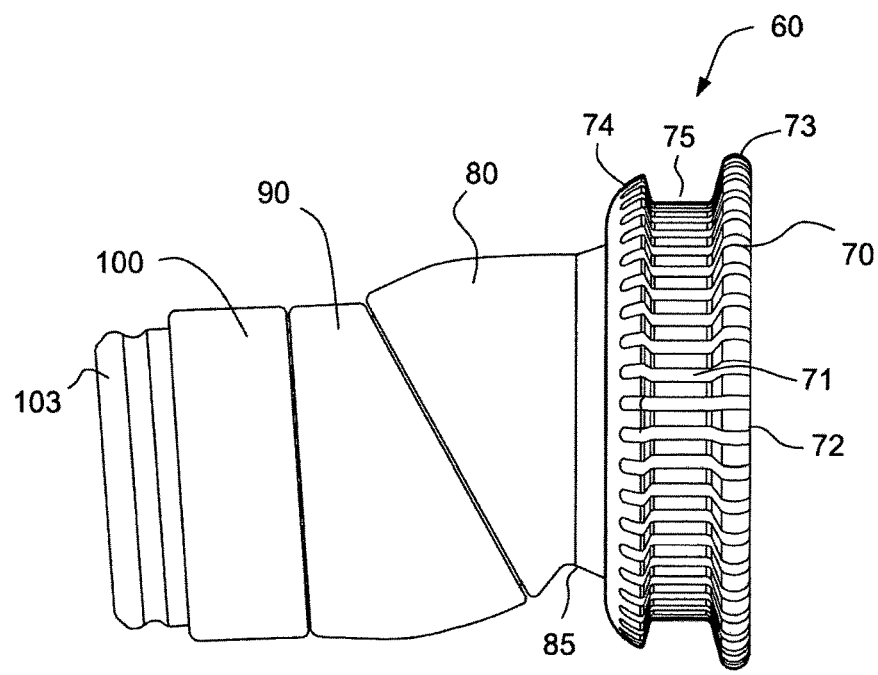
FIG. 22 is side view of the triple swivel elbow and connector assembly in the second position.
Figure 23:
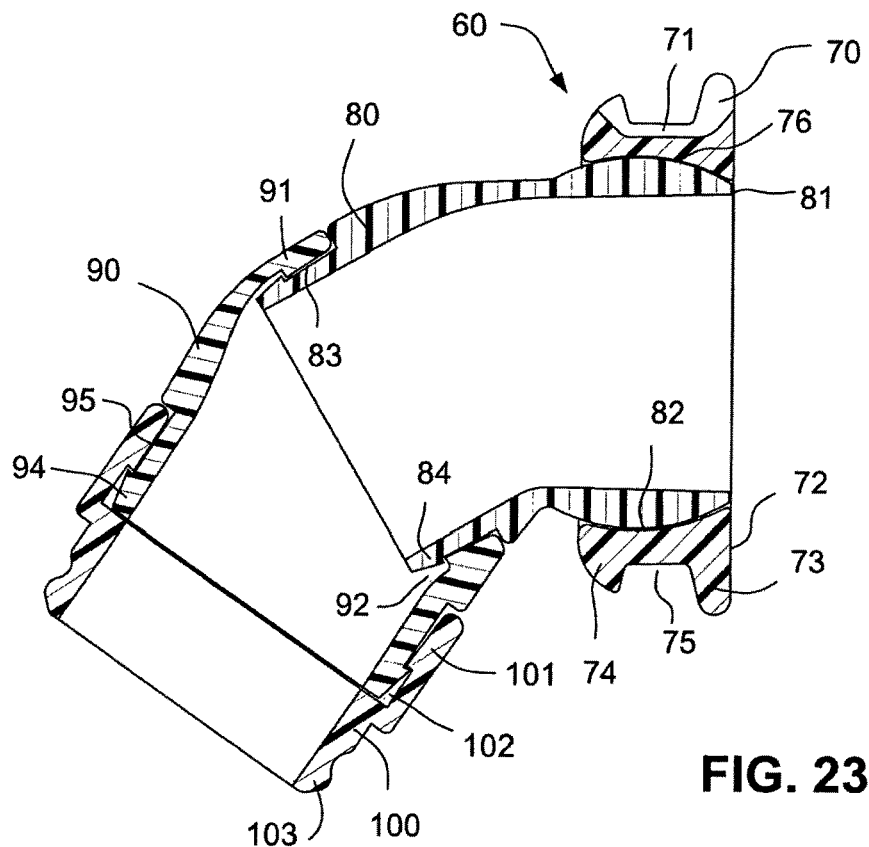
FIG. 23 is a cross sectional side view of the triple swivel elbow and connector assembly in the first position.
Figure 24:
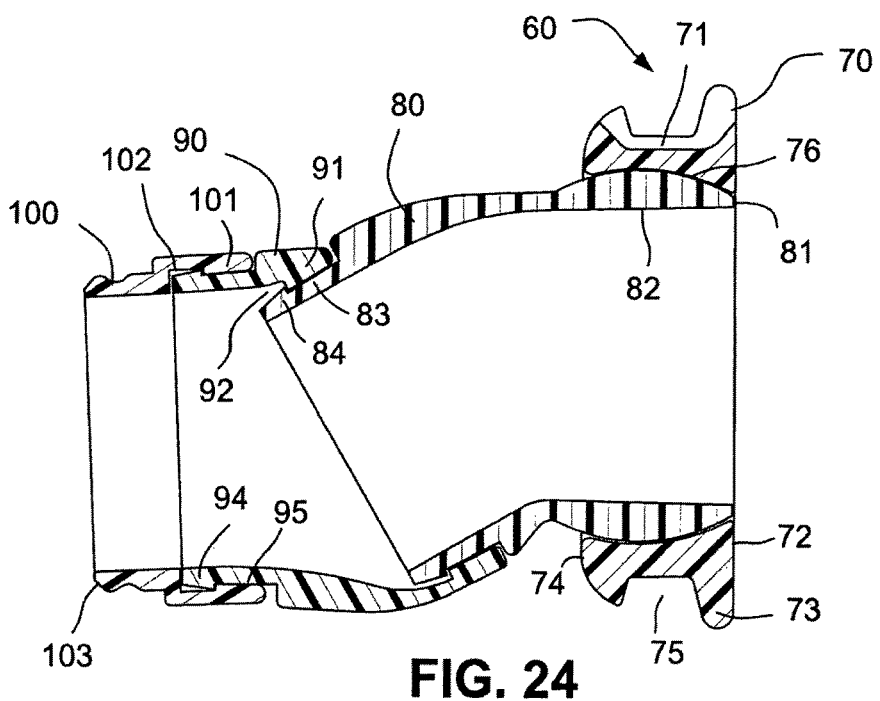
FIG. 24 is a cross sectional side view of the triple swivel elbow and connector assembly in the second position.
Figure 25:
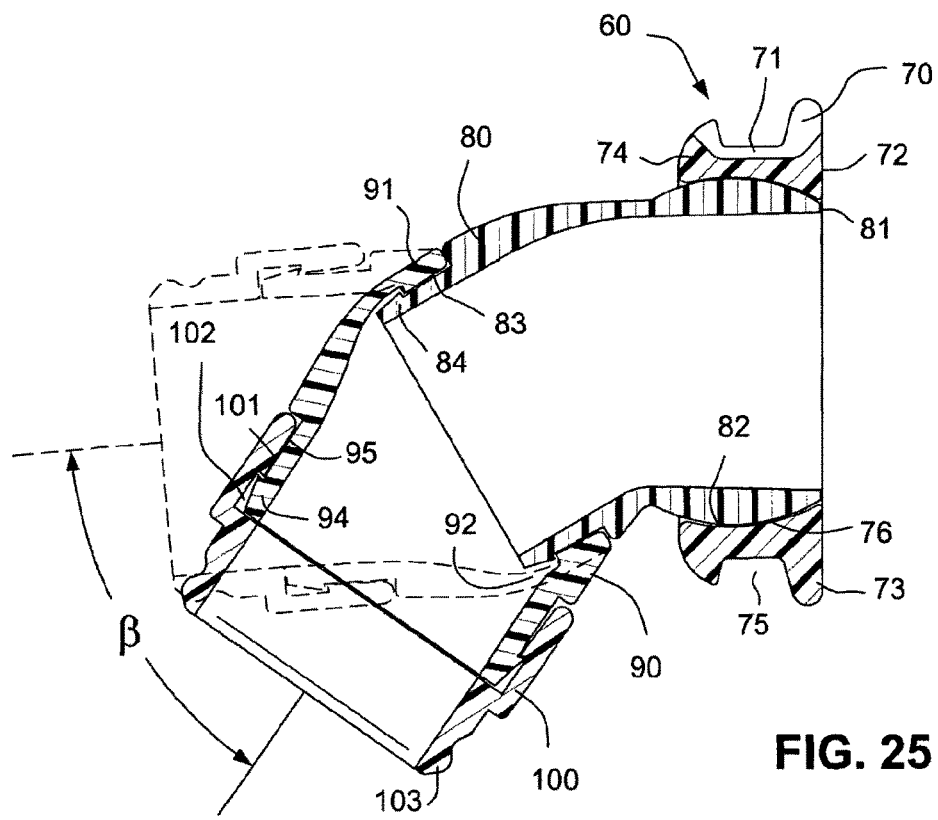
FIG. 25 is side view of the transition of the triple swivel elbow and connector assembly from the first position to the second position.
Figure 26:
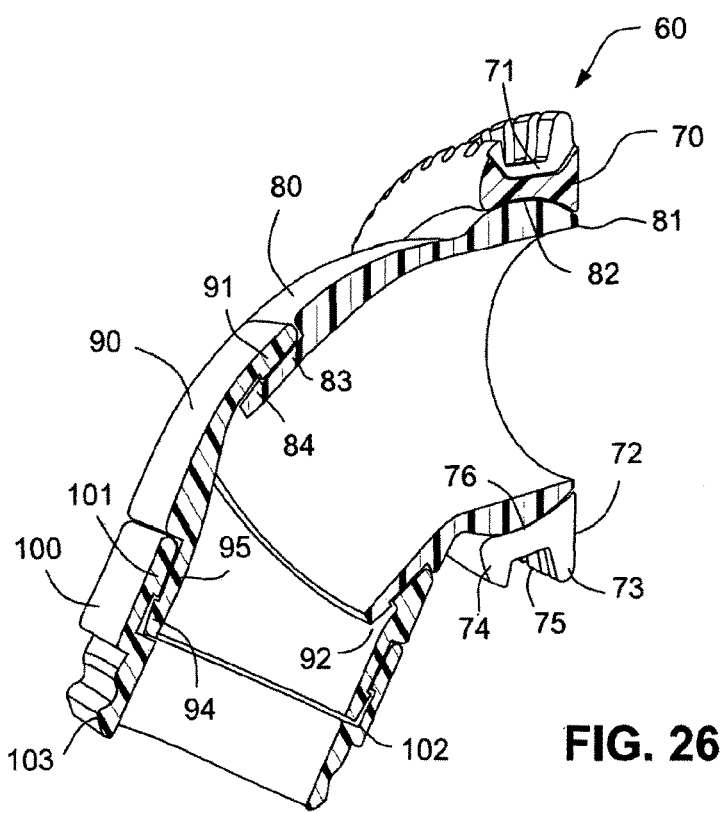
FIG. 26 is a cross sectional isometric view of the triple swivel elbow and connector assembly in the first position.
Figure 27:
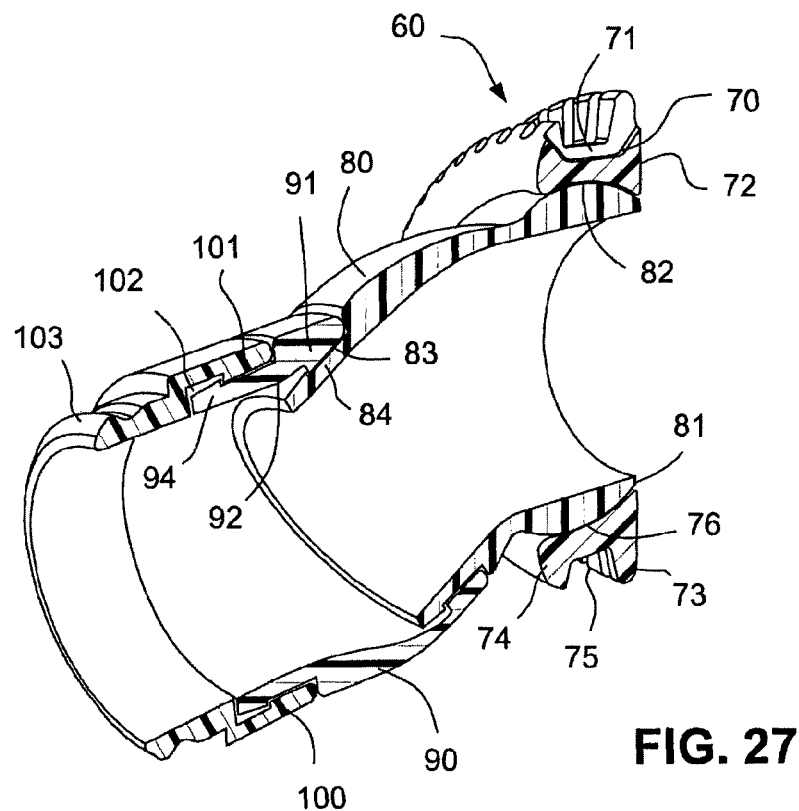
FIG. 27 is a cross sectional isometric view of the triple swivel elbow and connector assembly in the second position.
Figure 28:
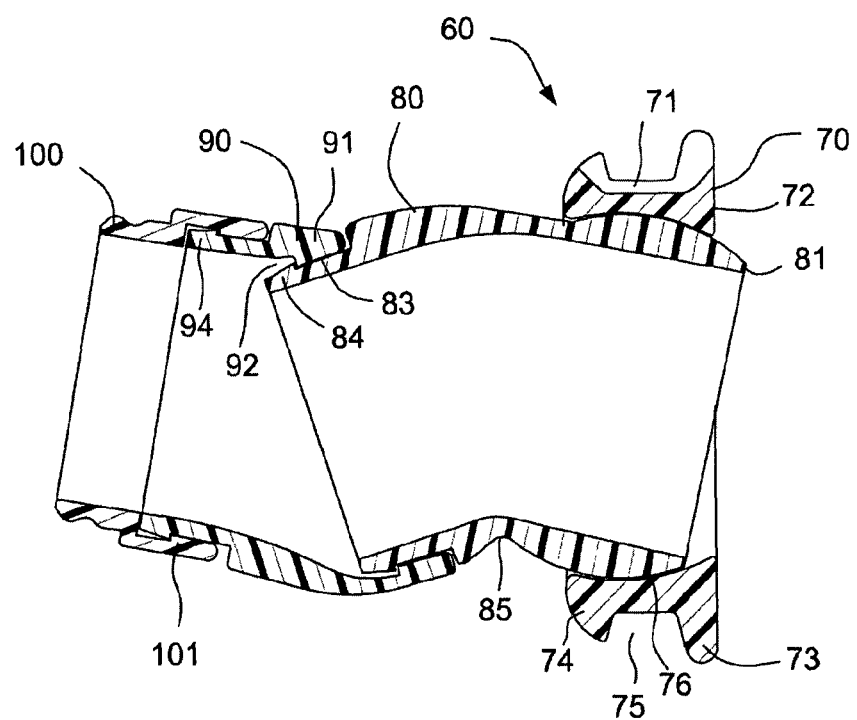
FIG. 28 is a cross sectional side view of the triple swivel elbow and connector assembly in a third position or configuration.
Figure 29:
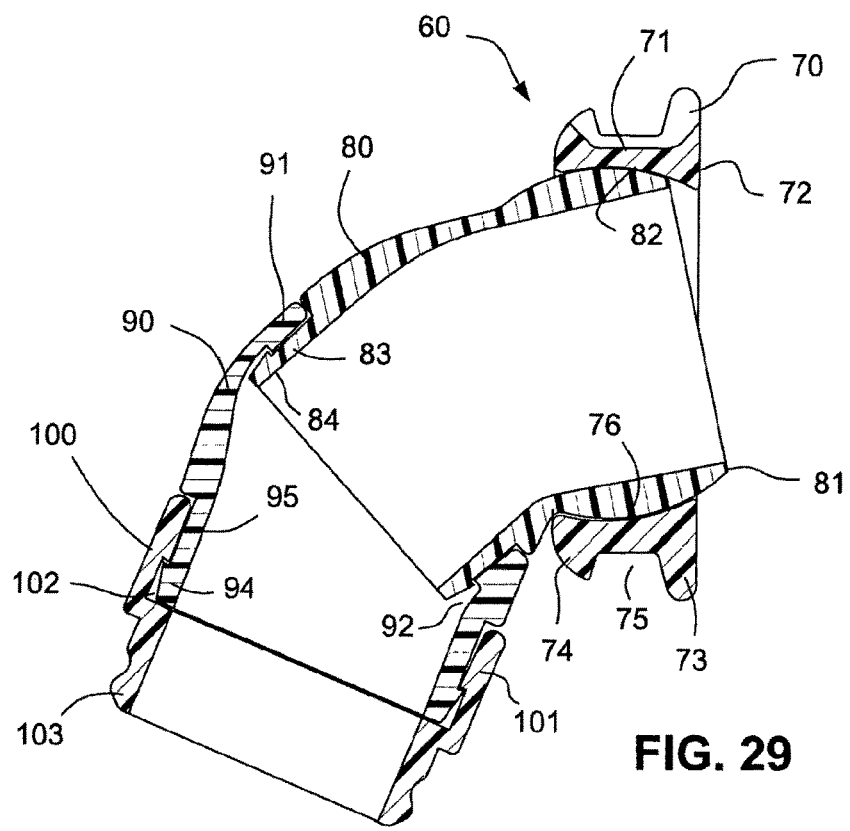
FIG. 29 is a cross sectional side view of the triple swivel elbow and connector assembly in a fourth position or configuration.
Figure 30:
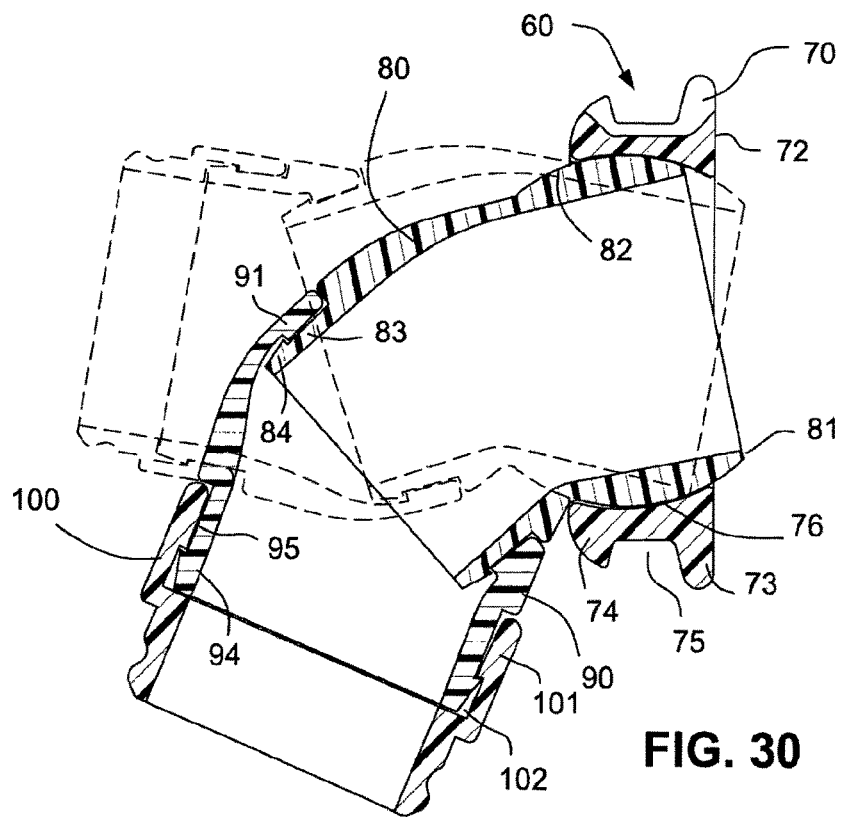
FIG. 30 is a cross sectional side view of the transition of the swivel elbow and connector assembly from the third position to the fourth position.

The swivel cuff 90 and the swivel elbow 80 of the examples shown in FIGS. 17-30 are swivelable in the same manner as described with respect to the example disclosed in FIGS. 5-16. As shown in FIGS. 21 and 25, the pivoting of the swivel cuff 90 allows a longitudinal axis of the triple swivel elbow and connector assembly 60 to rotate through an angle β of, for example, 40-60°, for example 50°. Although the second swivel cuff 100 is shown as including an annular groove 102 that receives the tapered flange 94 of the swivel cuff 90, it should be appreciated that the second swivel cuff 100 may be provided with an angled groove similar to, the angled groove 92 of the first swivel cuff 90 to permit the second swivel cuff 100 to swivel through an angle similar to the manner in which the swivel cuff 90 swivels with respect to the swivel elbow 80.

Swivel Elbow and Anti-Asphyxia Valve Assembly

Referring to FIGS. 38-47, a swivel elbow and anti-asphyxia valve assembly 300 according to an example of the technology may be provided having a diffuse vent. The assembly may also include engagement portions, e.g. buttons or actuators, for engaging and disengaging the assembly 300 to a patient interface, e.g. a mask. The assembly 300 may be molded in one piece. This arrangement is advantageous as the patient is not required to dismantle the component (thereby preventing potential loss of components or misalignment when reassembling), the cost of the component may be lower, and the anti-asphyxia valve may be positioned such that it cannot be tampered with or accidentally removed.

Figure 38:
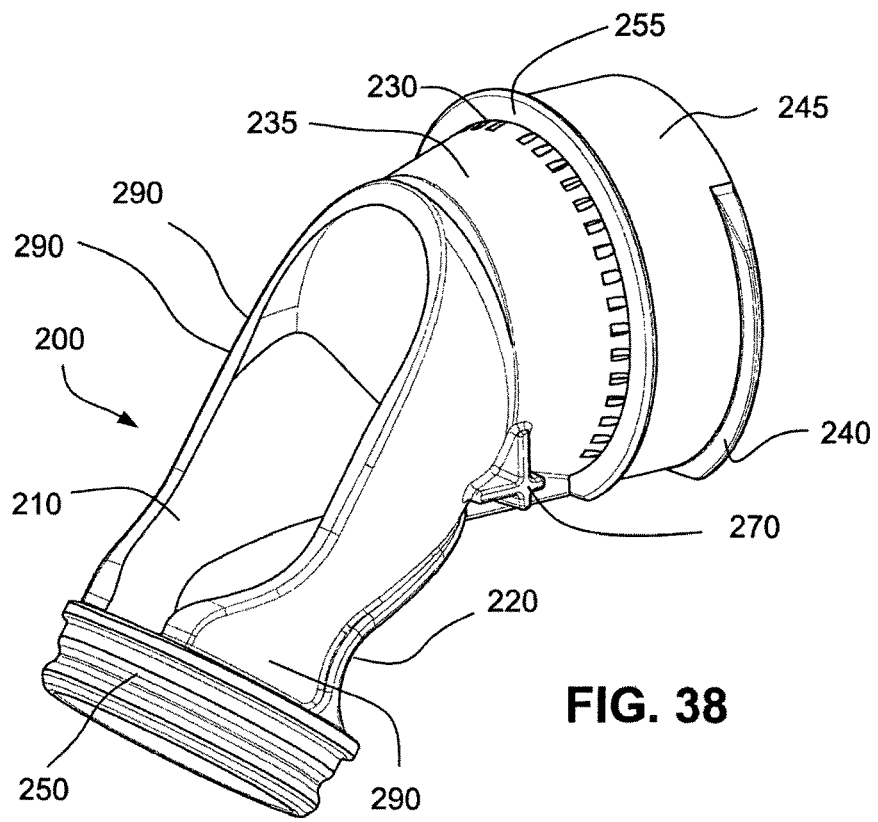
FIG. 38 is an isometric view of a first component of a swivel elbow and anti-asphyxia valve assembly according to an example of the technology.
Figure 39:
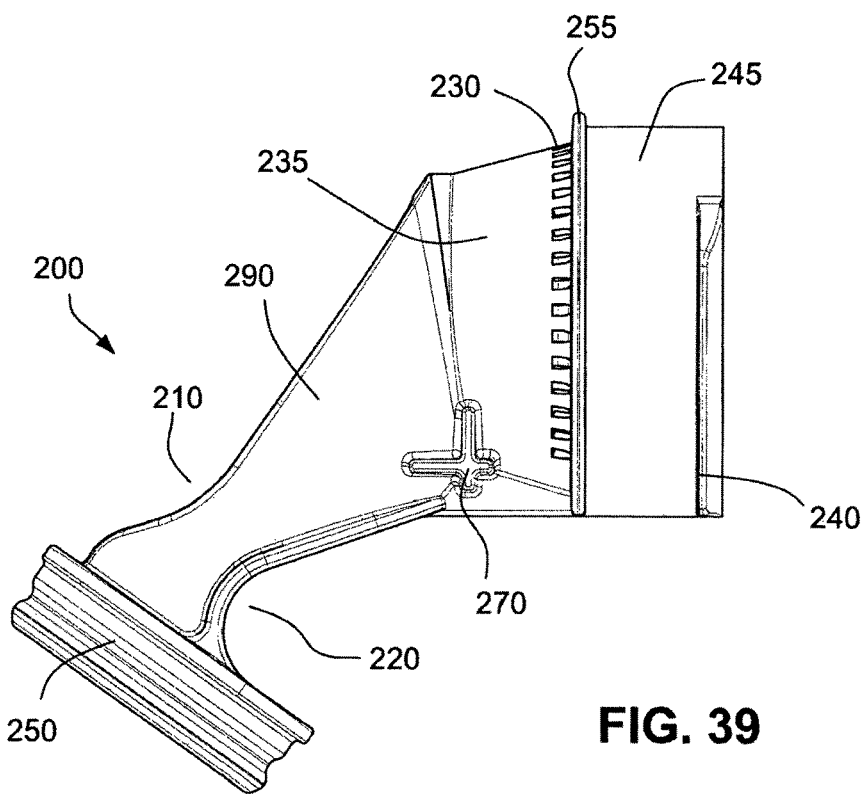
FIG. 39 is a side view of the first component of FIG. 38.
Figure 40:
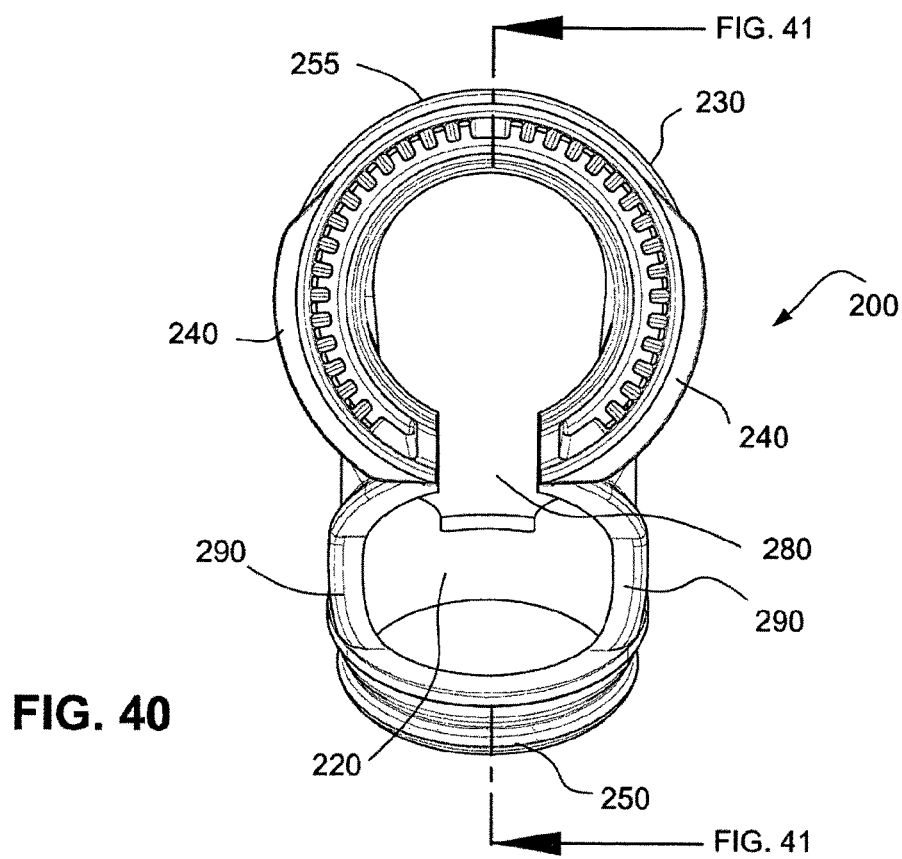
FIG. 40 is a rear view of the first component of FIGS. 38 and 39.
Figure 41:
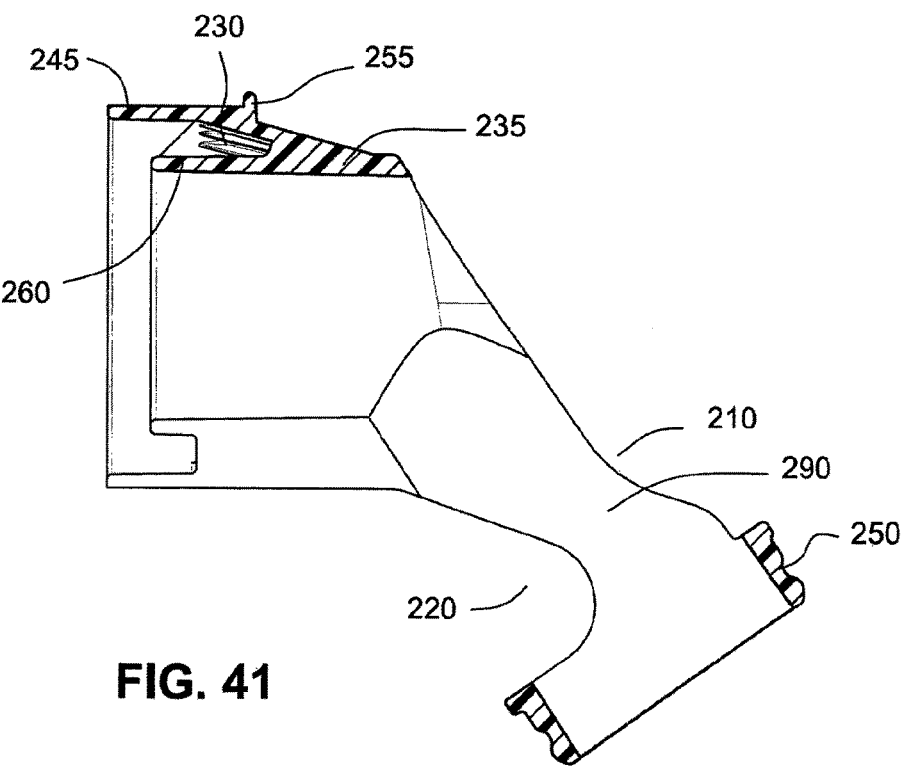
FIG. 41 is a cross sectional side view of the first component of FIGS. 38-40.
Figure 42:
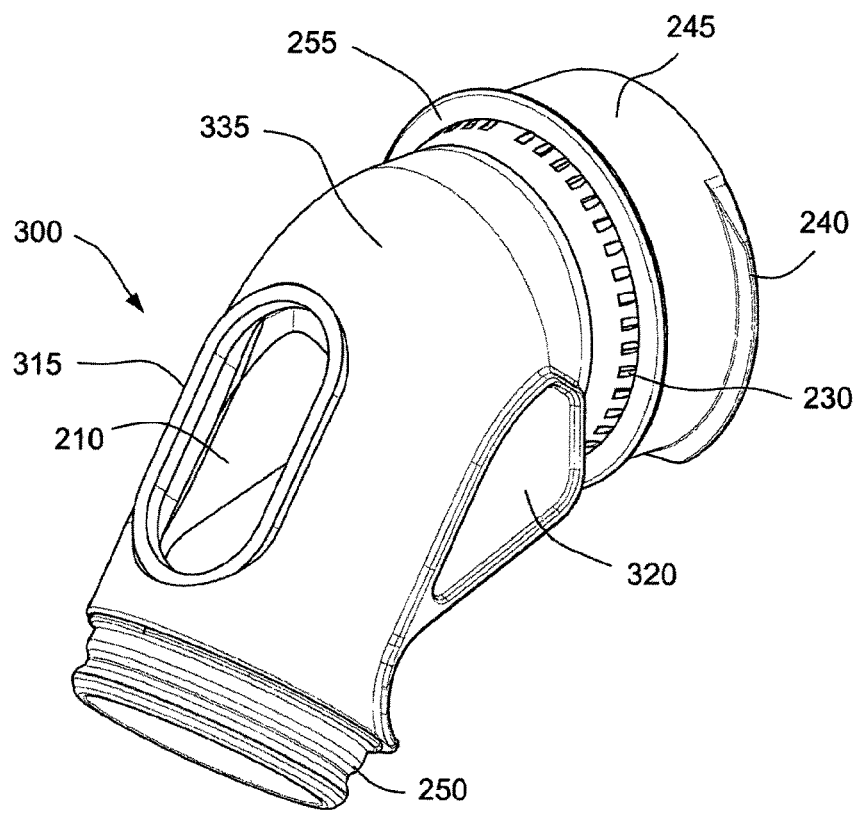
FIG. 42 is an isometric view of the first component and a second component of the swivel elbow and anti-asphyxia valve assembly.
Figure 43:
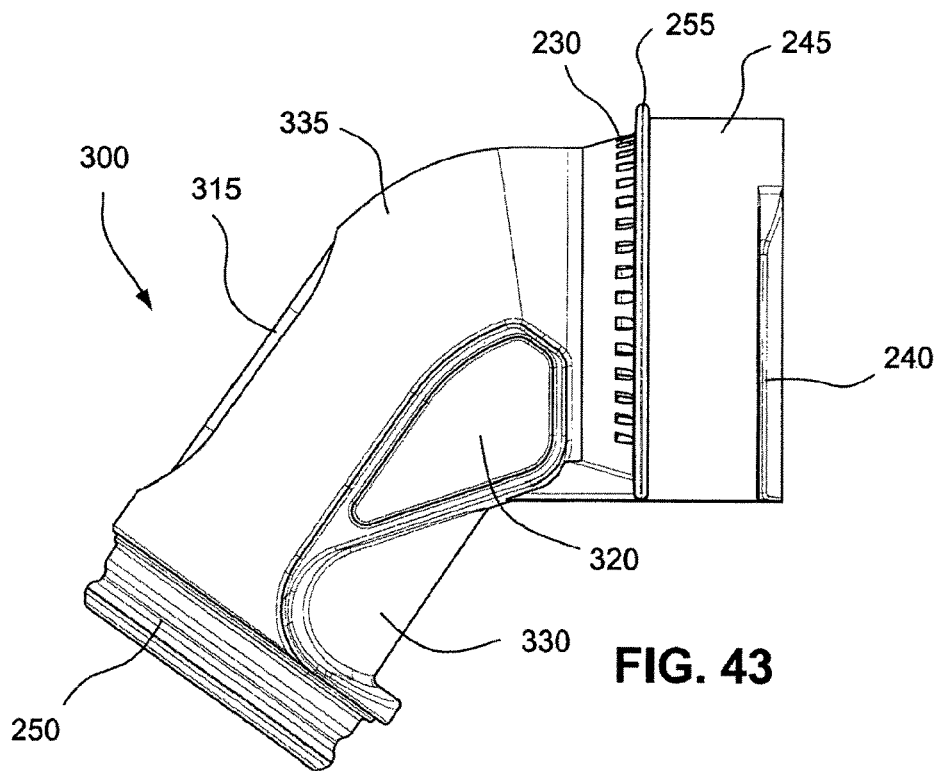
FIG. 43 is a side view of the swivel elbow and anti-asphyxia valve assembly of FIG. 42.
Figure 44:
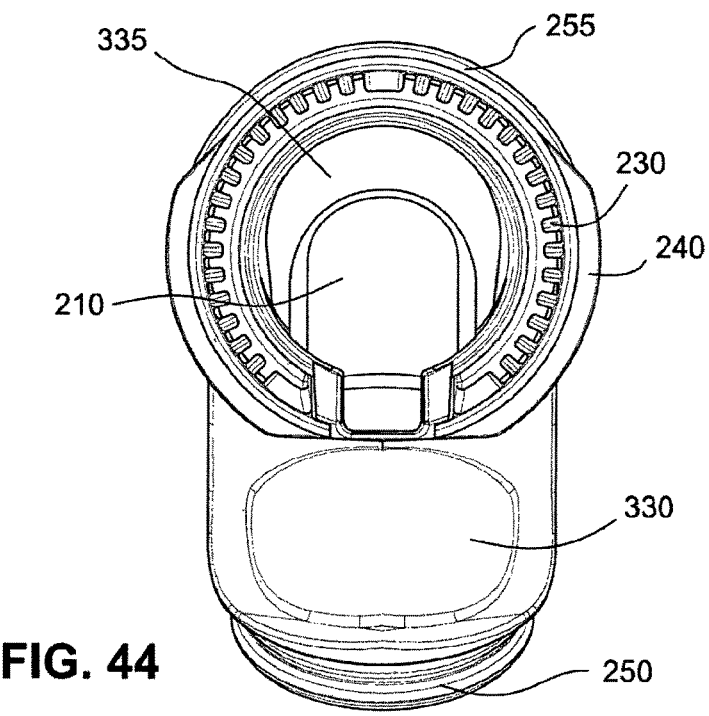
FIG. 44 is a rear view of the swivel elbow and anti-asphyxia valve assembly of FIGS. 42 and 43.
Figure 45:
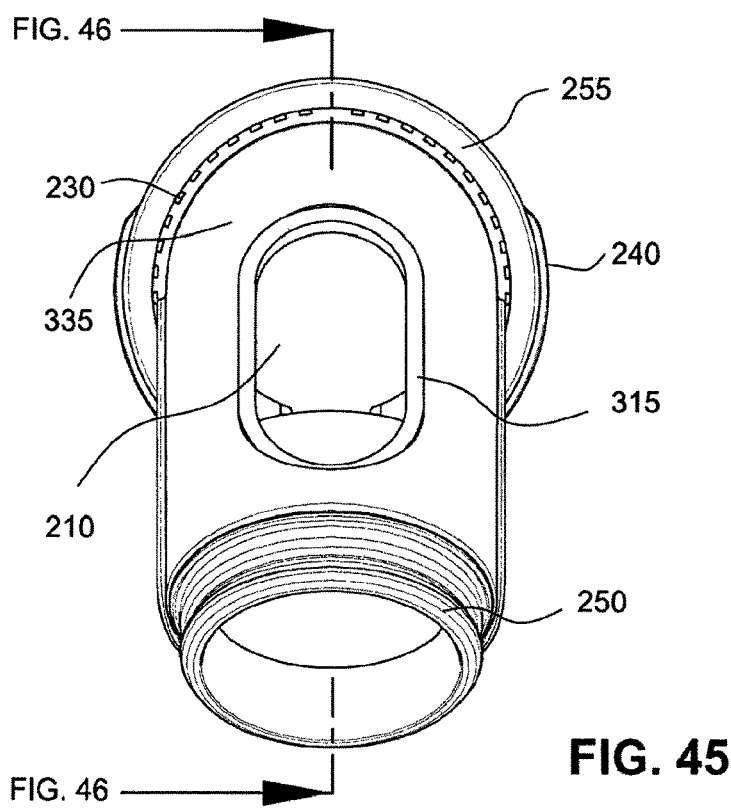
FIG. 45 is a front view the swivel elbow and anti-asphyxia valve assembly of FIGS. 42-44.

The assembly 300 may comprise a first elbow component, base moulding, collar or skeleton portion 200, as shown in FIGS. 38-41. The skeleton portion 200 may provide the underlying structure of the assembly 300 to support the assembly in an open or patent position. As shown in FIG. 38, the skeleton portion 200 may include vent holes 230 adapted to permit the exit of exhausted gases from a patient interface as per previously described examples. As shown in FIG. 41, the skeleton portion 200 may further comprise a baffle 260 adapted to separate the incoming gases from the outgoing gases in the assembly 300 as per previously described examples.

The skeleton portion 200 may also include a first connection region 245 comprising engagement tabs 240 for interfacing or connecting with a patient interface, for example. The first connection region 245 may be substantially arcuate or define a first arcuate region when viewed from the front. The skeleton portion 200 may also include a second connection region 250 for interfacing or connecting with a tube or swivel, for example. The skeleton portion 200 may further include a stop 255 to position the assembly 300 with respect to a mask, for example, and prevent the assembly 300 from travelling through the connection with the mask or insertion of the assembly 300 into the mask.

The skeleton portion 200 may be formed of a relatively rigid, or stiff, material so that the structure may remain open to permit the flow of gases. Stiffer materials may minimize the noise of the air exiting the vent holes. The skeleton portion 200 may be formed of, for example, polycarbonate, polypropylene, or nylon. A rigid material may also assist in maintaining the assembly 300 in an open position under certain loads, e.g. the patient lying on the assembly. A rigid material may also be easier for the user to connect and disconnect from the mask, tube and/or swivel.

As shown in FIG. 39, the skeleton portion 200 may further comprise supports, arms or interconnecting regions 290 adapted to connect the first connection region 245 with the second connection region 250. The supports 290 may also form the boundaries of a first aperture 210 and a second aperture 220. The supports 290 may be flexible and resilient, i.e. the supports 290 may return to their original shape after deformation. The first aperture 210 may be structured and arranged to receive an anti asphyxia valve or other valve. The second aperture 220 may be structured and arranged to receive a flexible member or web. The second aperture 220 may extend to an opening, gap or relief 280 at the first connection region 245, as shown in FIG. 40.

Referring to FIG. 39, the vent holes 230 may be positioned on a surface 235 that is generally circular or rounded to better diffuse exiting air streams. The surface 235 may be tapered to prevent moisture build up on the elbow—this can cause vent whistle i.e. air exiting the vent holes to create a high pitched whistle-like noise. The vent holes 230 may be scattered around the surface 235 to diffuse the air flow. It should be appreciated that the vent holes 230 may be uniformly spaced around the surface 235, or provided as otherwise described herein.

The skeleton portion 200 may further include second supports or stops 270 adapted to receive a button or other engagement mechanism. The second supports 270 may be adapted to transmit a force from an engagement feature or mechanism, such as a button, to the skeleton portion 200. The second supports 270 may also reinforce or provide a foundation for an engagement feature or mechanism, such as a button, such that when the button is pressed it does not collapse, rather it transmits a force to the skeleton portion 200. The second supports 270 may be an alignment feature to align the skeleton portion 200 in a tool or mold. The second supports 270 may form a surface for a second component, for example an over-mould, to abut or be formed against.

The skeleton portion 200 may be over-moulded or otherwise formed with a second component (also referred to as a flexible portion or deformable region) 335, e.g. an assembly over-mould. For example, the skeleton portion 200 may be moulded in a first tool and then transferred to a second tool for over-moulding with the second component 335, or could be done all in one tool. That is, second component 335 may be chemically, mechanically or otherwise formed to the skeleton portion 200. The second component 335 may be formed of a relatively flexible material, such as thermoplastic elastomer (TPE), silicone, gel or other material.

The second component 335 may include engagement portions 320, a flexible member or web 330, a lip 315 and a valve member 310. The engagement portions 320 may be, for example, buttons, grips, tabs or other arrangements adapted to receive a pressing force or other motion from a patient or clinician. The engagement portions 320 may be supported and/or reinforced by the second supports 270. The engagement portions 320 may, when pressed, squeeze towards one another thereby displacing the first supports 290 inwards. The first supports 290 may then deform the first connection region 245 from a first, resting position (e.g. a circular shape) to a second, pressed position (e.g. an oval or elliptical shape). The gap or relief 280 may be adapted to permit the first connection region 245 to flex. This change in shape may move the engagement tabs 240 from a first, engaged position, to a second, disengaged position. The gap or relief 280 may form a second arcuate region, such that when combined with the first arcuate region of the first connection region 245, the two components form a circle and hence a cylinder.

The flexible member or web 330 may be connected to the engagement portions 320 and also seal the second aperture 220. The flexible member 330 may be in the form of a membrane or other readily deformable shape, as when engagement portions 320 are pressed, the flexible member 330 may buckle or bend.

The lip 315 may be formed about and positioned around the perimeter of the first aperture 210. The lip 315 may be adapted to prevent objects from entering the first aperture 210. The lip 315 may also serve as a blank off for molding elbow assembly 300.

Figure 46:
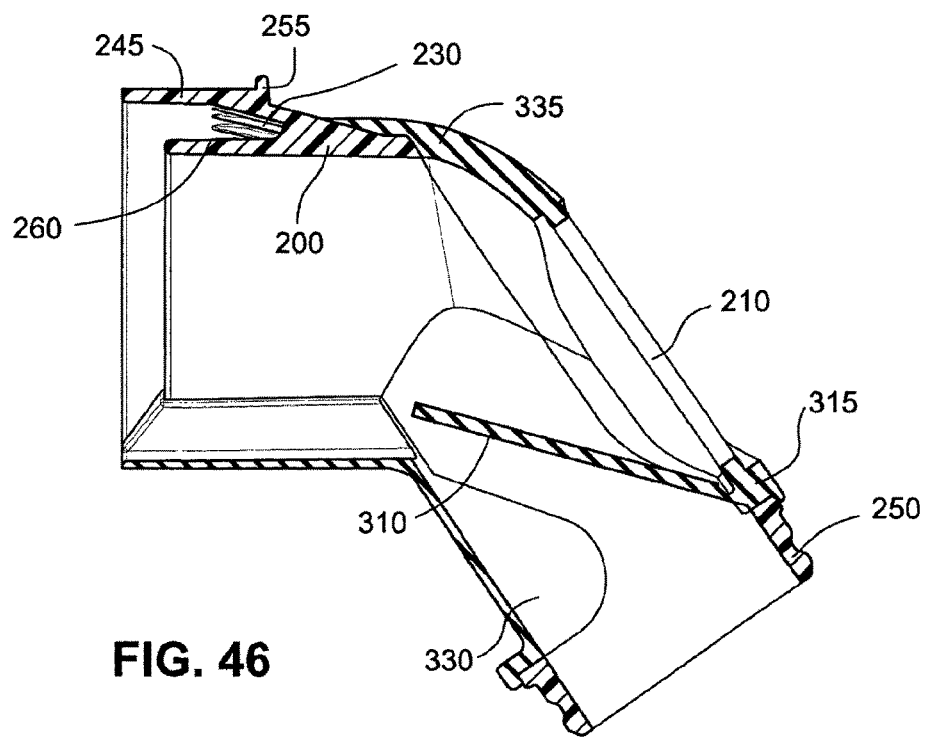
FIG. 46 is a cross sectional side view of the swivel elbow and anti-asphyxia valve assembly of FIGS. 42-45.
Figure 47:
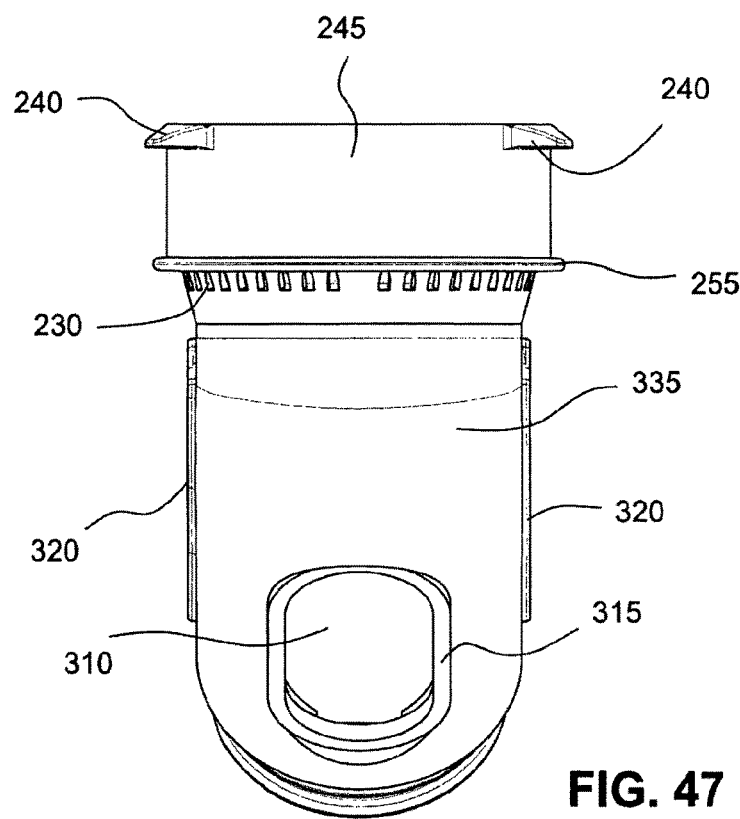
FIG. 47 is a top view of the swivel elbow and anti-asphyxia valve assembly of FIGS. 42-46.

The valve member 310, as shown in FIG. 46, may be positioned within the body of the elbow assembly 300, i.e. between the first supports 290. The valve member 310 may act as an anti-asphyxia valve, i.e. when air is delivered from the second connection region 250 to the first connection region 245, the valve member 310 may move into a first position (not shown) to occlude the first aperture 210; and when there is no air being delivered from the second connection region 250 to the first connection region 245, the valve member 310 may move to a second position (FIG. 46) that does not occlude the first aperture 210, thereby permitting the patient to receive air from atmosphere through the first aperture 210. The valve member 310 may be a flap. The valve member 310 may be integrally formed with the second component 335, e.g. through a living hinge attached to the lip. It should be appreciated that the valve member 310 may be formed separately from the second component 335 and attached to the second component 335. The valve member 310 may be larger than the first aperture 210, so as to occlude the first aperture 210 when air is delivered from the second connection region 250 to the first connection region 245.

The valve member 310, the lip 315, the engagement portions 320, and the flexible member 330 may be formed from the same material in a single piece. Alternatively, one or more of these components may be formed separately and/or from an alternative material.

In a further example of the present technology, e.g., shown in FIGS. 68A-70 an elbow 80 may be formed or constructed in a multi-step process, e.g., three step process, to achieve a single component with multiple functions. The elbow 800 may comprise a skeleton or frame 805, e.g., constructed of rigid or semi-rigid material, and adapted to communicate air flow from an air delivery tube to a mask. The skeleton 805 may be first formed or molded in a tool. Skeleton 805 may be constructed of a polymer such as polypropylene, polycarbonate, and nylon.

Figure 69A:
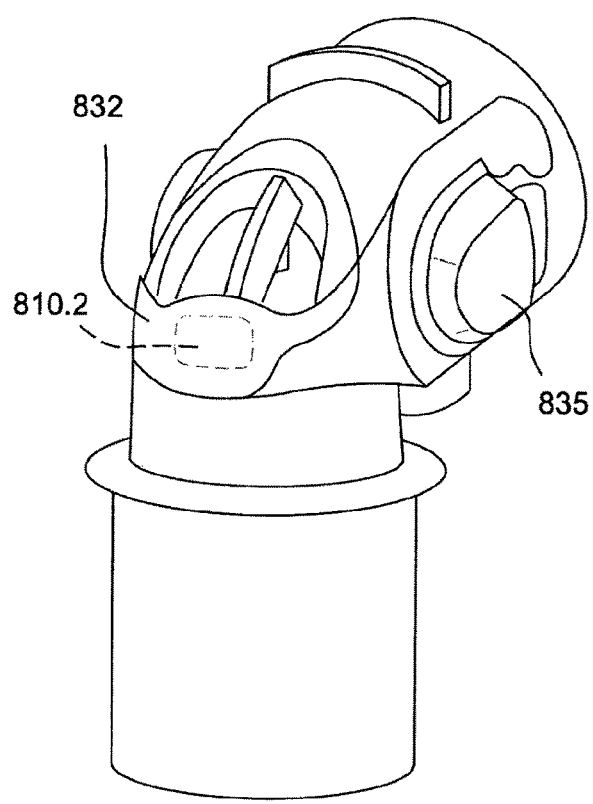
FIG. 69A shows a perspective view of the a variant of the elbow.
Figure 69B:
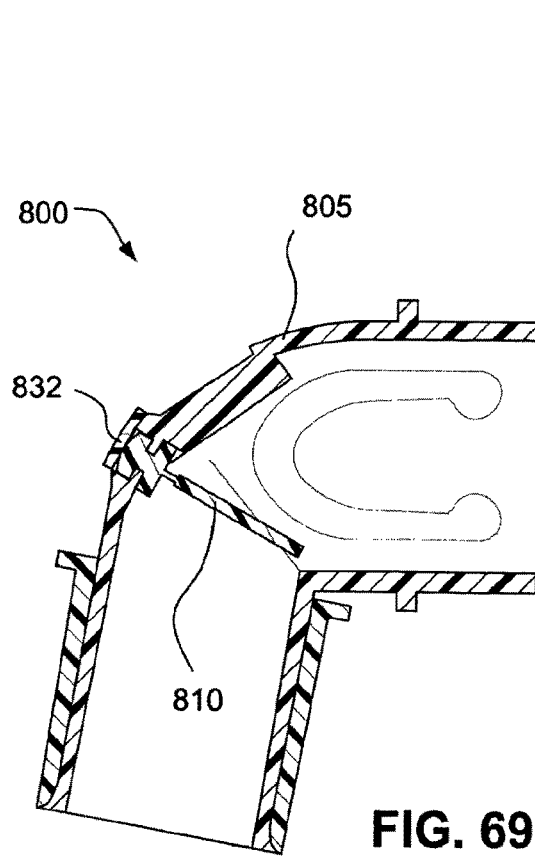
FIG. 69B shows a cross section of the variant shown in FIG. 69A.
Figure 70:
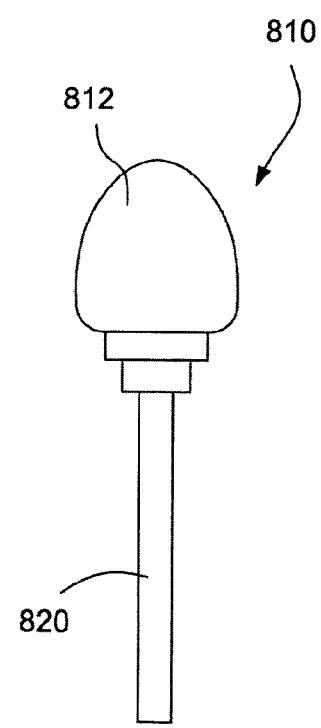
FIG. 70 shows the AAV (a variant) in isolation.

The elbow 800 may further comprise an AAV (anti-asphyxia valve) 810 having a flap 812 adapted to provide the patient with access to atmospheric gas should a flow generator fail to deliver air to the mask. The AAV 810 may be formed or molded within the skeleton 805 or formed or molded and then subsequently assembled to the skeleton 805. For example, as shown in FIGS. 68A-68D, the AAV 810 may be molded and then pulled through an opening 815 in the skeleton. A pull tab 820 of the AAV may enable the AAV 810 to be pulled through the opening 815 so as to position, retain and/or seal the AAV relative to the skeleton. The pull tab 820 may be a sacrificial component that once utilized (e.g., pulled through the opening) it may be cut off (such that an outer surface 810.2 of an outer flange 810.1 is substantially flush with the elbow surface) as shown in FIG. 69 or otherwise removed (e.g., once an inner flange 825 is pulled and anchored against the inner surface of the skeleton, further applied force will tear the pull tab away from the AAV, possibly assisted by a perforation(s) between pull tab and outer flange 810.1). Alternatively the AAV 810 may be molded in the opening 815 and extending through the skeleton 805 without the need for pull tab 820. The AAV 810 may include an inner flange 825 to seal the AAV 810 against the inner wall 830 of the skeleton 805.

The elbow 800 may comprise a flexible component 832 (FIG. 69A) adapted to secure the AAV 810 in position and/or form one or more release buttons 835 of the elbow 800. For example, the flexible component 832 may be a silicone or TPE which is molded over the skeleton 805 to form the outer portions of the release buttons 835, thereby allowing the release buttons 835 to flex; and may be molded over the AAV 810 at the opening 830 to seal and hold the AAV 810 in position relative to the skeleton 805.

The arrangement may have one or more of the following advantages:
  The AAV is sealed in position and cannot be removed from the elbow thereby preventing the patient from accidentally disassembling the AAV and thus rendering the device unsafe.
  The flexible component can be molded in a single shot—if there was no flexible component over the AAV then the flexible component may be molded on either side of the elbow at each button. Since it is molded in a single shot, it may be more efficient and less expensive to tool
  The elbow may be more visually appealing.

Swivel Elbow and Connector Assembly Including Patient Interface Cushion

Figure 48:
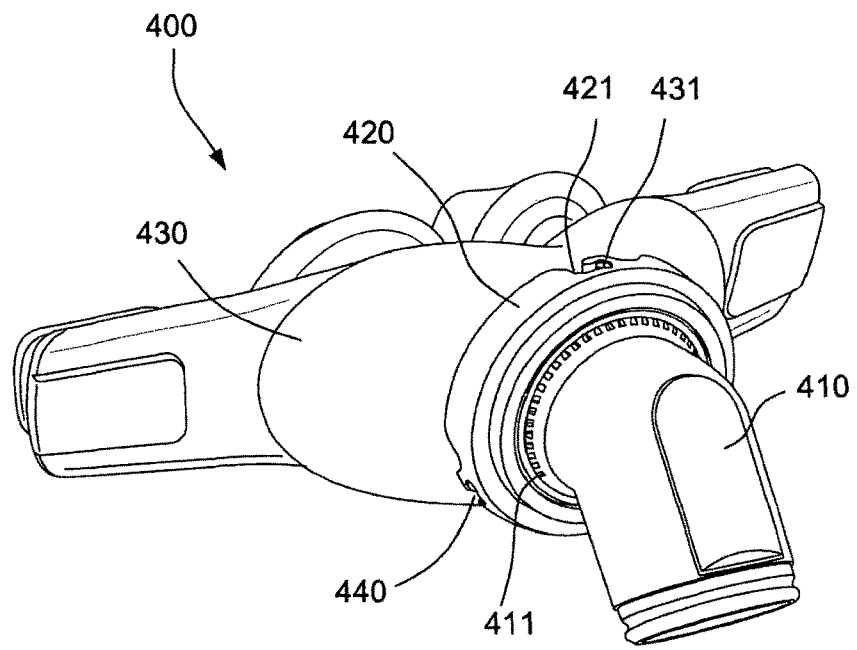
FIG. 48 is an isometric view of a patient interface including a swivel elbow and connector assembly according to another example of the technology.

Referring to FIG. 48, a patient interface system 400 for delivering a flow of breathable gas to a patient may include a swivel elbow 410, a swivel or ring or connector 420, and a cushion 430 for sealingly engaging the patient's airways. Although the cushion 430 as shown includes nasal pillows or prongs or puffs, it should be appreciated that other cushions may be provided, for example a nasal cushion or a full face cushion. The swivel 420 may be removably attachable to the cushion 430 by a bayonet type connection 440 that includes detents 421 on the swivel 420 to engage with tabs 431 on the cushion 430. Vents 411 are provided between the elbow 410 and the swivel 420. The vents 411 may include slots provided on the elbow surface to create venting gaps between the elbow 410 and the swivel 420. It should be appreciated that the slots may be provided in the swivel instead of the elbow, or that slots may be provided in both the elbow and the swivel.

Figure 49:
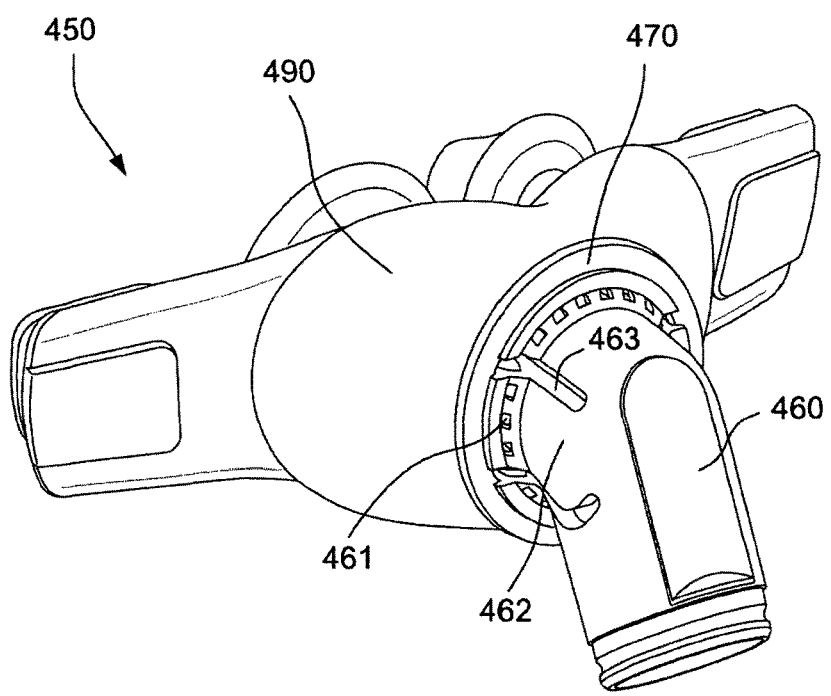
FIG. 49 is an isometric view of a patient interface including a swivel elbow and connector assembly according to another example of the technology.
Figure 50:
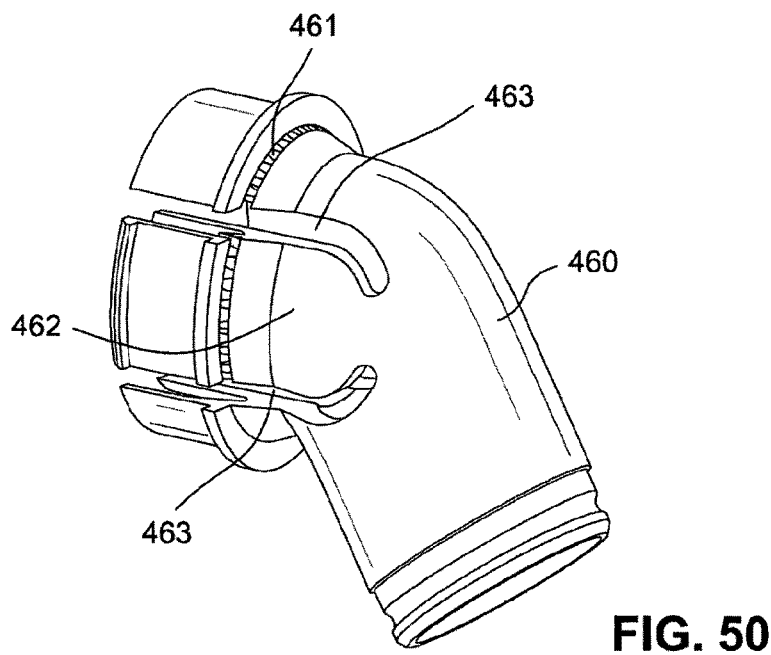
FIG. 50 is an isometric view of the elbow of FIG. 49.
Figure 51:
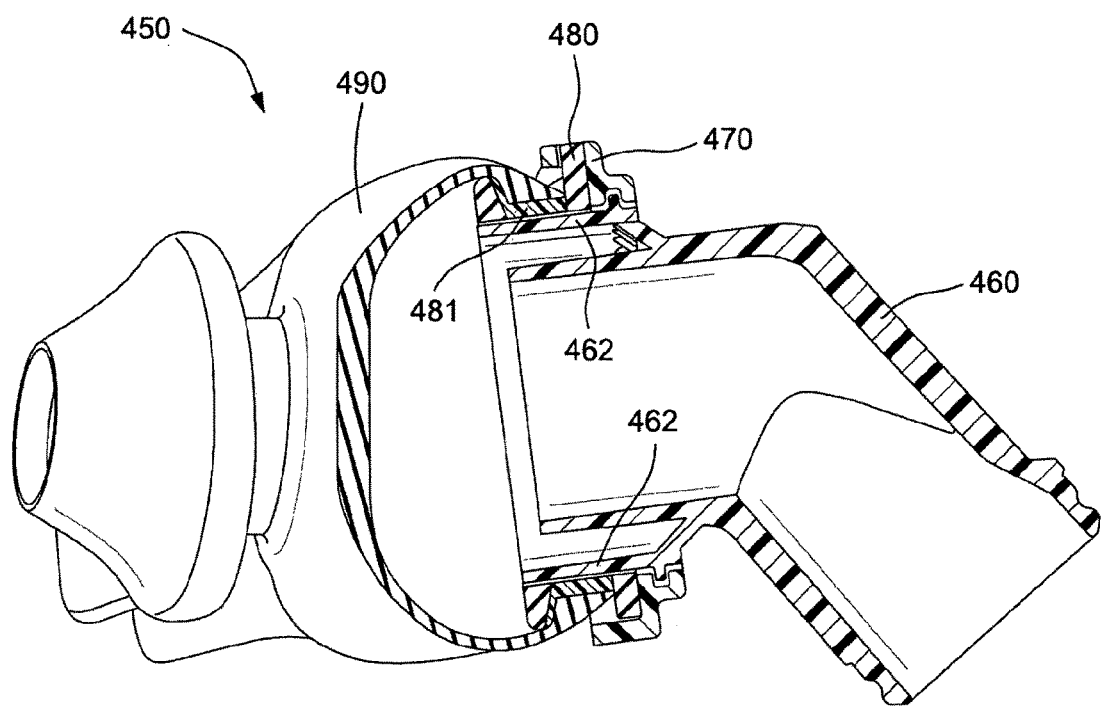
FIG. 51 is a cross sectional view of the patient interface of FIG. 49.

Referring to FIGS. 49-51, according to another example a patient interface system 450 may include a swivel elbow 460, a swivel or ring or connector 470, and a cushion 490. The swivel 470 may be connected to a ring 480 that is attached to the cushion 490 at 481. The ring 480 may be permanently or removably attached to the cushion 490. For example, the cushion 490 may be overmoulded to the ring 480 or the cushion 490 and the ring 480 may be attached by adhesive. As another example, the cushion 490 and the ring 480 may be press fit together.

The elbow 460 may be removably attached to the swivel 470 or the elbow may be permanently attached to the swivel 470. The elbow 460 may have flexible buttons 462 provided between grooves 463 formed in the elbow 460. The buttons 462 may be pressed or flexed to connect and disconnect the elbow 460 from the swivel 470.

Vents 461 are provided between the elbow 460 and the swivel 470. The vents 461 may include slots provided on the elbow surface to create venting gaps between the elbow 460 and the swivel 470. It should be appreciated that the slots may be provided in the swivel instead of the elbow, or that slots may be provided in both the elbow and the swivel.

Figure 52:
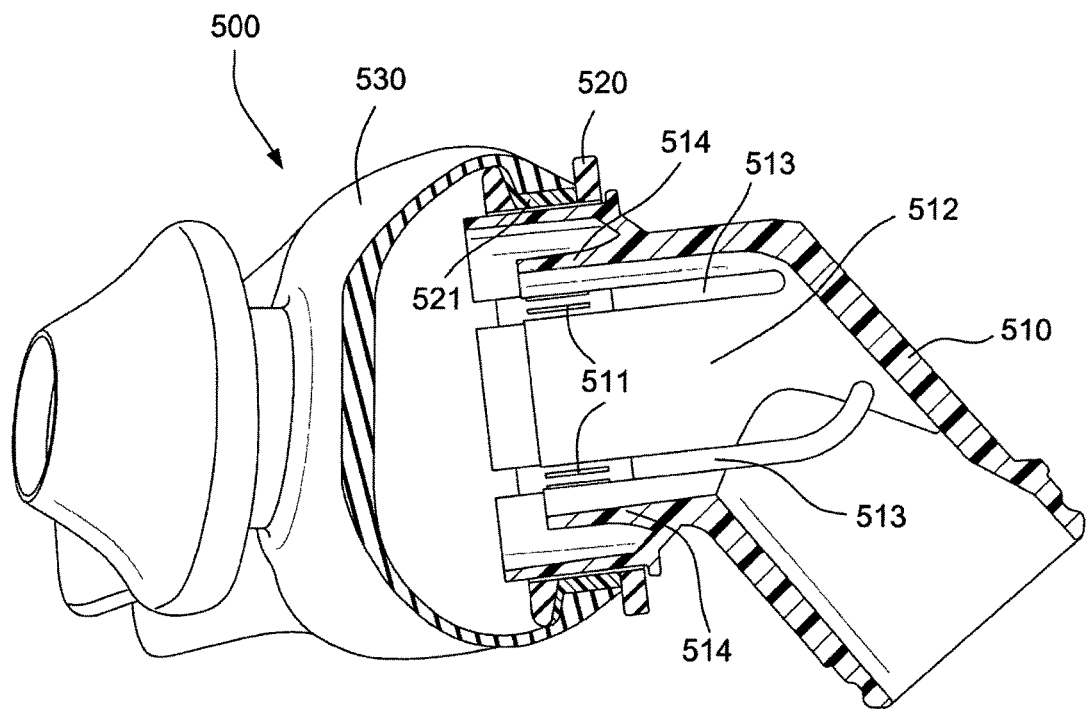
FIG. 52 is a cross sectional view of a patient interface including a swivel elbow and connector assembly according to another example of the technology.

Referring to FIG. 52, a patient interface system 500 according to another example may include a swivel elbow 510, a swivel or ring or connector 520, and a cushion 530. The cushion 530 may be permanently or removably connected to the swivel 520 at 521. The elbow 510 may be press fit to the swivel 520 and be releasable by pressing buttons 512 provided between grooves 513 as per grooves 463. Grooves 463 are made air tight by either being thinned regions of material or an over-molded second material (e.g., TPE, silicone). The elbow 510 may further include slots 511 to vent exhaled gases and a baffle 514 to reduce noise and increase exhaust gas washout.

Figure 53:
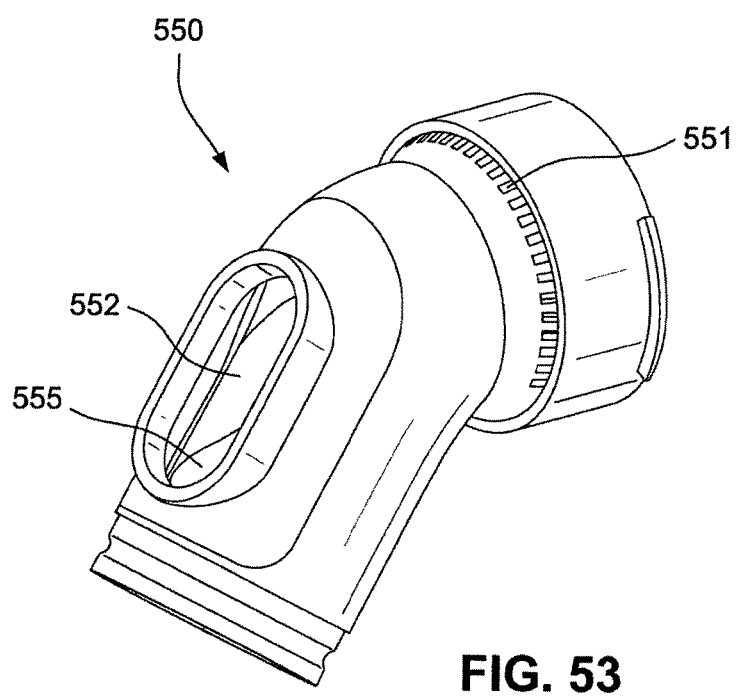
FIG. 53 is an isometric view of an elbow according to an example of the technology.
Figure 54:
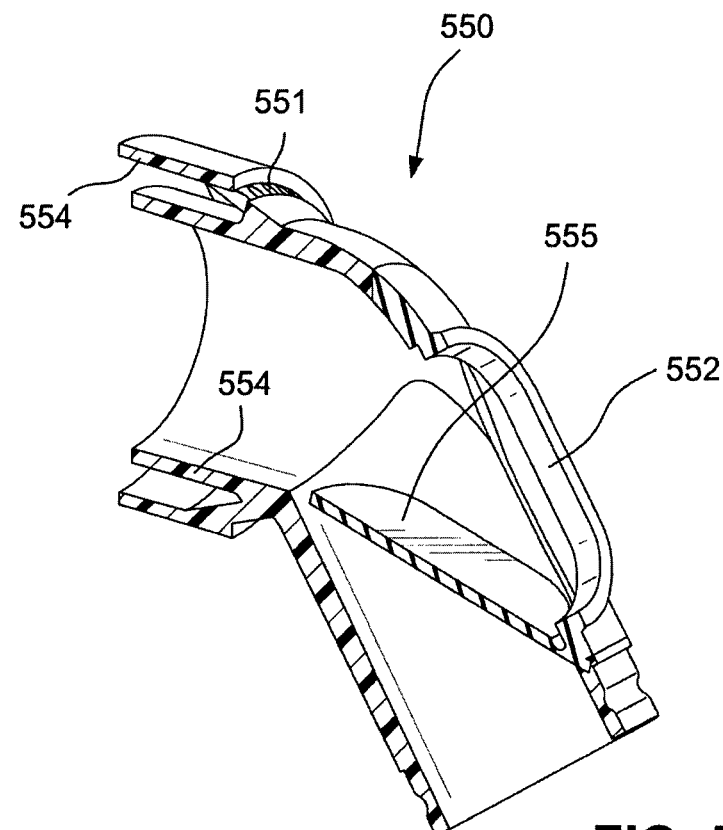
FIG. 54 is a cross sectional view of the elbow of FIG. 53.

Referring to FIGS. 53 and 54, an elbow 550 according to an example of the technology may include slots 551 to vent exhaled gases and a baffle 554 to reduce noise and increase exhaust gas washout. An aperture 552 may be provided in the elbow 550 to permit the patient to breathe in the event that the flow of breathable gas is interrupted or stopped. An AAV flap 555 is provided to close the aperture 552 when a flow of breathable gas is in the elbow 550 (i.e. the flow of breathable gas biases the flap 555 into a closed position to cover the aperture 552). As shown in FIGS. 53 and 54, the AAV flap 555 is in the open position. The elbow 550 may be moulded from, for example, a rigid material to improve vent flow noise and to prevent the slots 551 from occluding. The AAV flap 555 may be formed of, for example, a flexible material to enable movement of the AAV flap 555 from the open to the closed position under the influence of the flow of breathable gas.

Elbow and Tube Connector Assembly

Figure 55:
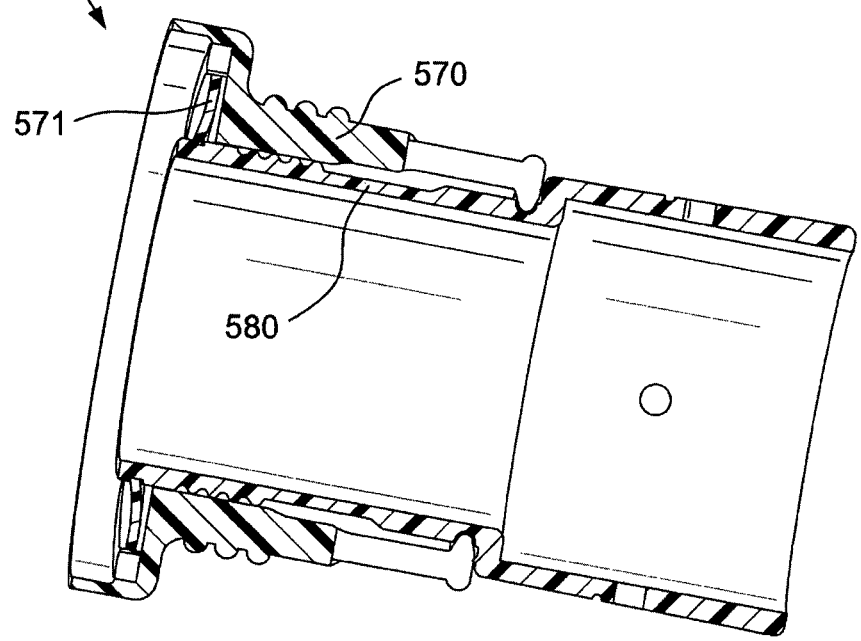
FIG. 55 is a cross sectional view of an elbow and tube connector assembly according to the technology.
Figure 56:
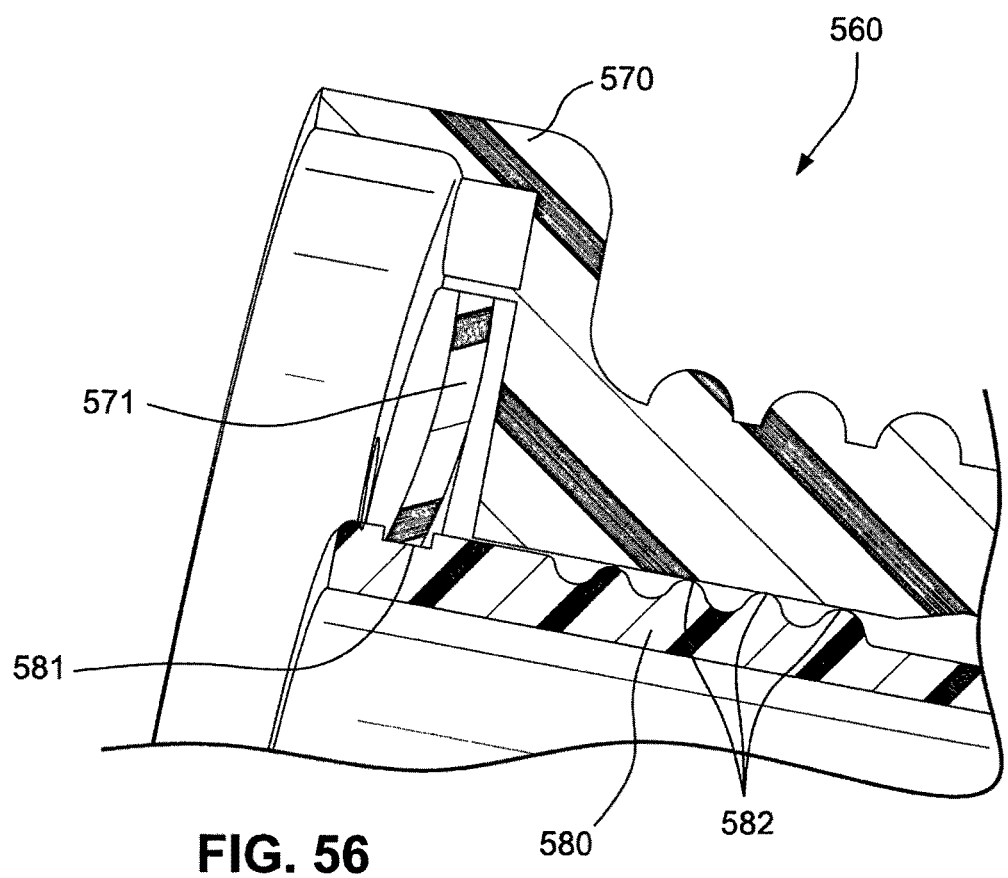
FIG. 56 is an enlarged view of a portion of FIG. 55.
Figure 57:
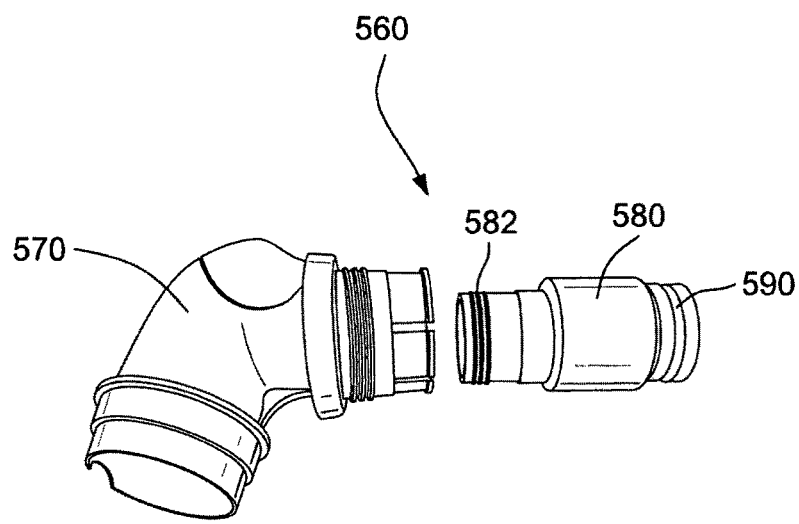
FIG. 57 is an exploded assembly view of the elbow and tube connector assembly of FIG. 55.

Referring to FIGS. 55-57, an elbow and tube connector assembly 560 may include an elbow 570 and a tube connector 580 that clips into the inner surface of the elbow 570. Clipping the tube connector 580 into the elbow 570 reduces the overall visual bulk of the assembly 560 and may also create a tube-specific fitting such that only tubes 590 provided by a certain manufacturer or provided can be used with the elbow 570.

The elbow 570 may include a lip or flexible element 571 adapted to engage with an outer surface, e.g. a groove, 581 of the tube connector 580 to ensure a more robust seal. The tube connector 580 may also include a series of ridges 582 adapted to engage with the inner surface of the elbow 570, thereby causing a seal, while avoiding increased friction between the tube connector 580 and the elbow 570 to permit rotation of the components relative to one another.

Straight Swivel for Elbow and Tube Connection

Figure 58:
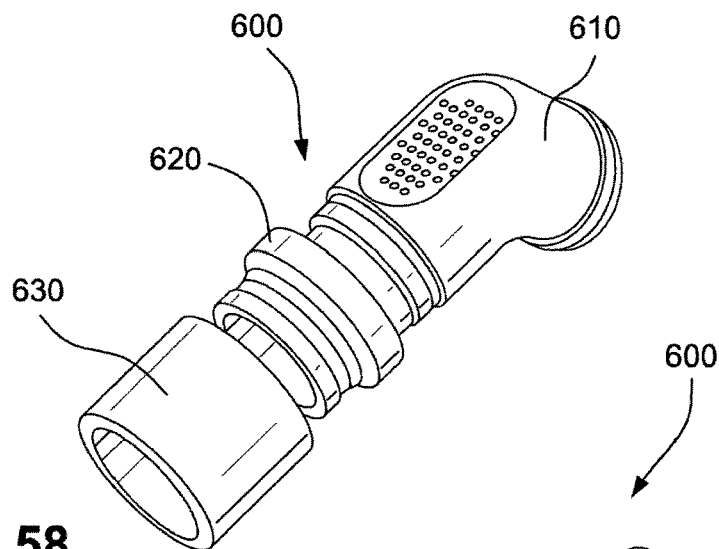
FIG. 58 is an exploded assembly view of an elbow and tube connector assembly according to another example of the technology.
Figure 59:
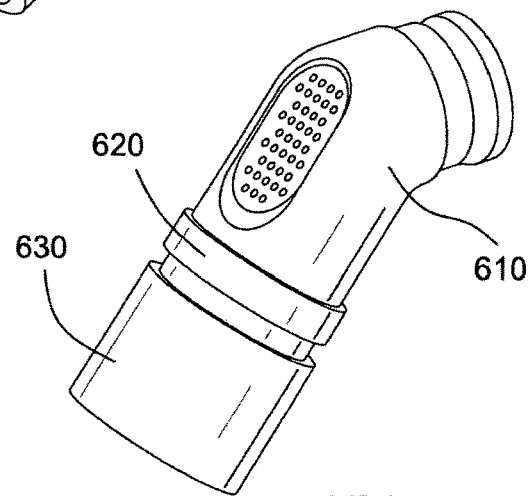
FIG. 59 is an assembly view of the elbow and tube connector assembly of FIG. 58.
Figure 60:
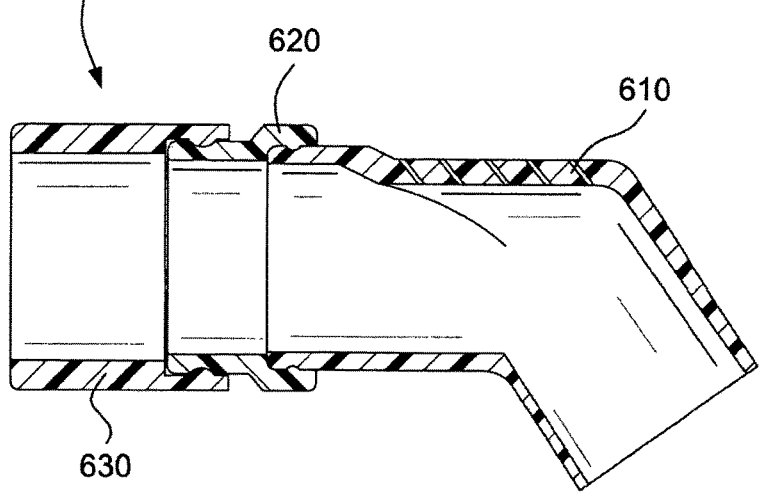
FIG. 60 is a cross sectional view of the elbow and tube connector assembly of FIG. 59.
Figure 64:
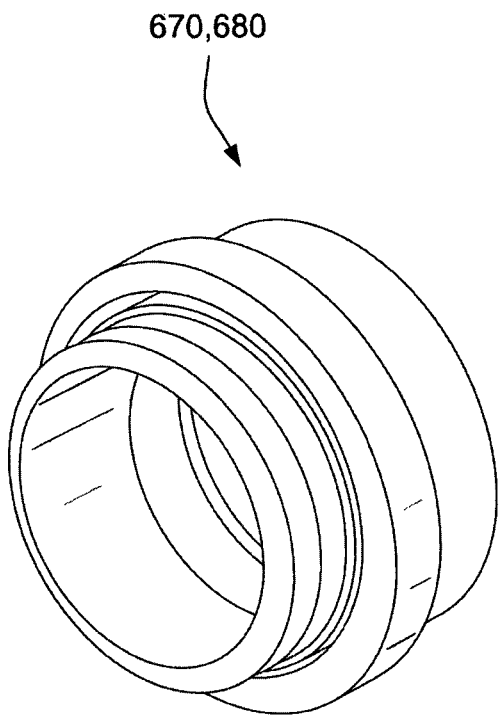
FIG. 64 is an isometric view of the connector of the elbow and tube connector assembly of FIG. 63.
Figure 65:
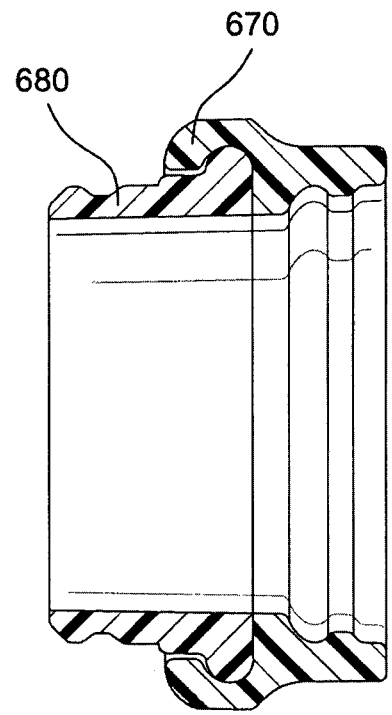
FIG. 65 is a cross sectional view of the connector of FIG. 64.

Referring to FIGS. 58-60, a tube and elbow connector assembly may 600 include a swivel elbow 610, a tube connector 630 and a swivel or connector or ring 620. The assembly 600 may be used to connect the elbow 610, such as the elbow disclosed in, for example, U.S. 2010/0307502 A1, the entire contents of which are incorporated herein by reference, to a short retractable tube, having a length of, for example 150 mm, such as disclosed in, for example, U.S. 2009/0078259 A1, the entire contents of which are incorporated herein by reference. The assembly 600 may reduce rotational/torque forces between the tube and the elbow. For example, as disclosed in U.S. 2010/0000534 A1, a patient interface system may include a "pillow cushion" that is adhesively applied to the patient's face. As the patient interface system has no headgear, it therefore has little to no resistance to rotational forces being applied to the pillow cushion. The patient interface system may include a decoupling gusset, a ring elbow and a short, retractable tube attached to the elbow. A longer tube, e.g. a 2 m tube, may be connected to the short, retractable tube by a swivel. As the short, retractable tube is stretched, it may rotate almost a full revolution. This in turn rotates the elbow and distorts the pillow cushion and may pull the prongs or pillows out of the nose. In the patient interface of U.S. 2010/0000534 A1, the short, retractable tube assembly is designed to be 'semi-permanent' and have minimal leak through the tube-elbow interface. As such, there is no ability to rotate at the short, retractable tube and elbow interaction site and the elbow acts as a solid fixture and increases the torque onto the cushion.

By altering the location of the swivel in the patient interface system, for example by placing the swivel between the short, retractable tube and the elbow, all the rotational forces of both the longer tube and the short, retractable tube would be rotationally decoupled from the cushion.

By copying the geometry of the external surface of the elbow, and the internal surface of the short tube cuff and offsetting each by, for example, 0.2 mm, preferably 0.1 mm, there would be clearance between both parts. As the tube is stretched and starts to rotate, the surface with the least resistance will swivel. The swivel may either 'fuse' (i.e. not rotate) on one side, and rotate 100% on the other, or take up 50% of the rotation on either side so that the cushion would only experience a tensile force.

Referring to FIGS. 61-65, a tube and elbow connector assembly 650 according to another example includes an elbow 660 connectable to a tube or tube cuff 690 by a swivel component 670, 680 made by, for example, overmoulding a first swivel component 680 over a second swivel component 670 in a mould assembly to form a freely rotating swivel in a smaller footprint, i.e. minimising the extension of the elbow length. The internal geometry of the cuff 690 and the external geometry of the elbow 660 were replicated to ensure a tight fit with no leak, yet the shrinkage of the in-mould assembly would allow a smooth rotation. The swivel components 670, 680 form a two part swivel moulded as one.

Figure 66:
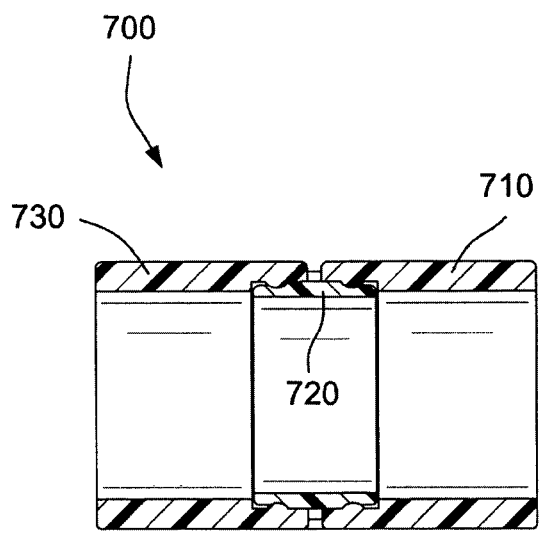
FIG. 66 is a cross sectional view of a tube connector assembly according to an example of the technology.
Figure 67:
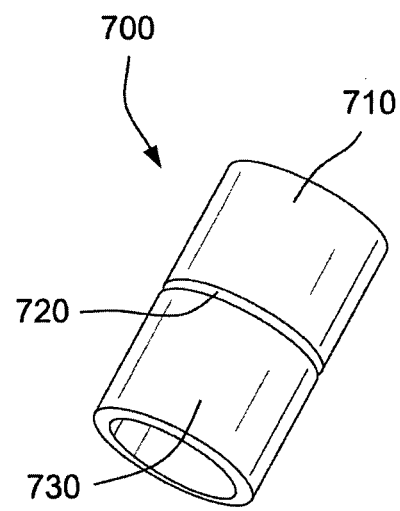
FIG. 67 is an isometric view of the tube connector assembly of FIG. 66.
Figure 68A:
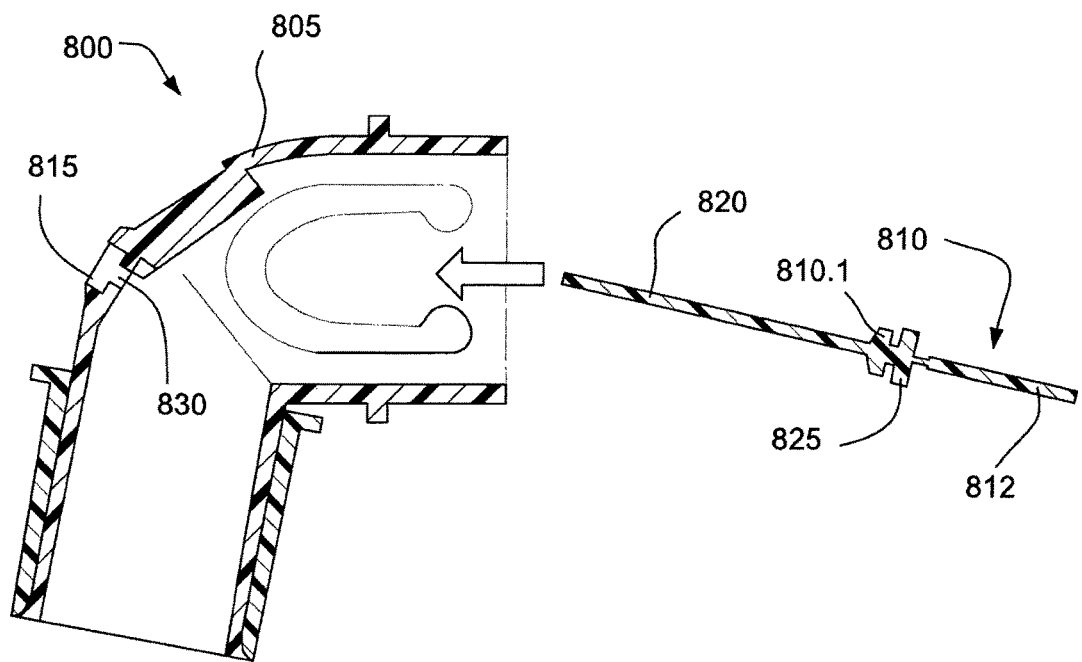
FIGS. 68A-D show a multi-step process for manufacturing an elbow with anti-asphyxia valve.
Figure 68B:
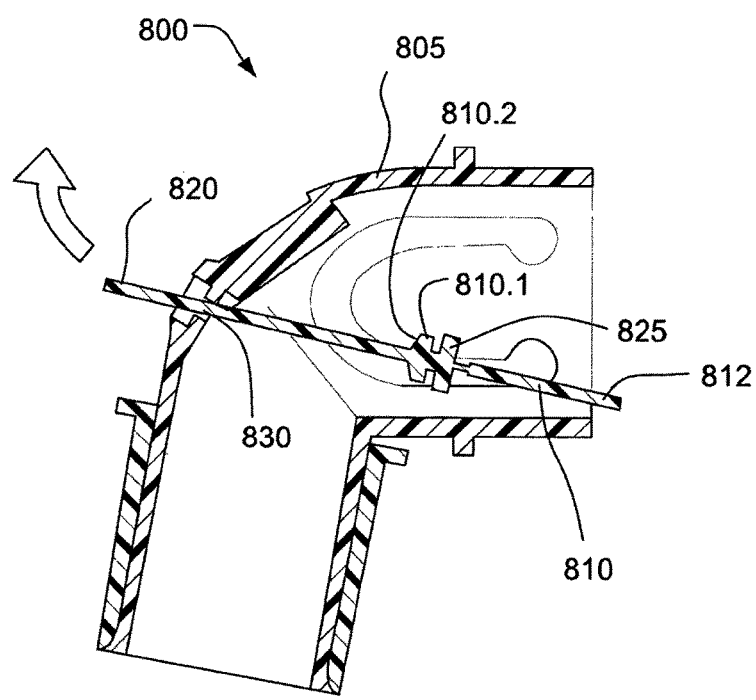
Figure 68C:
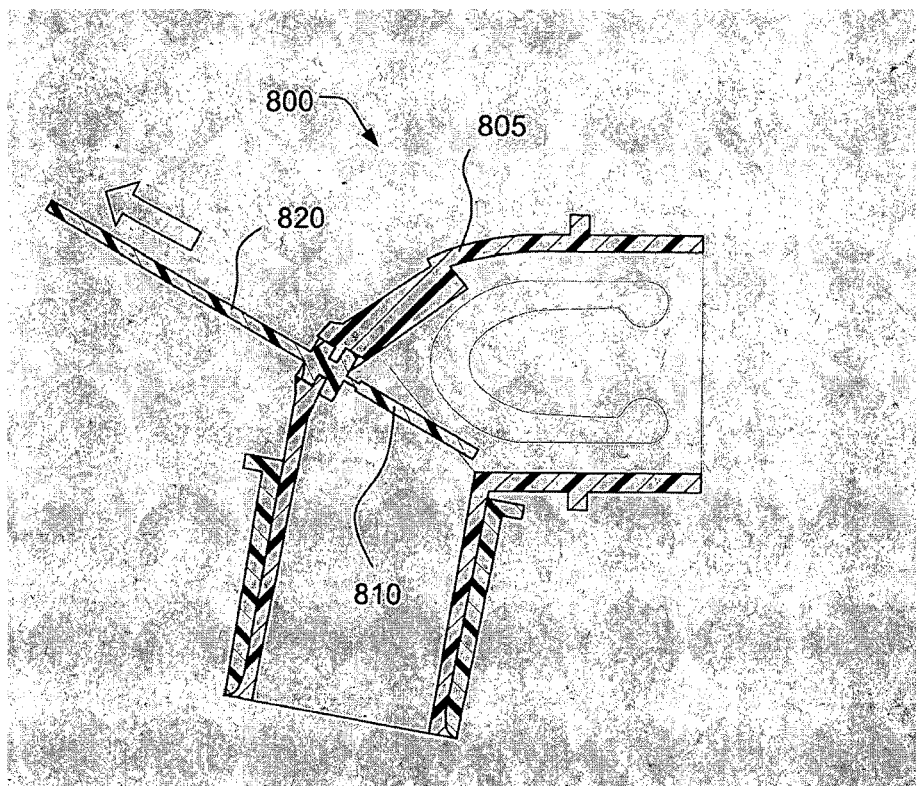
Figure 68D:
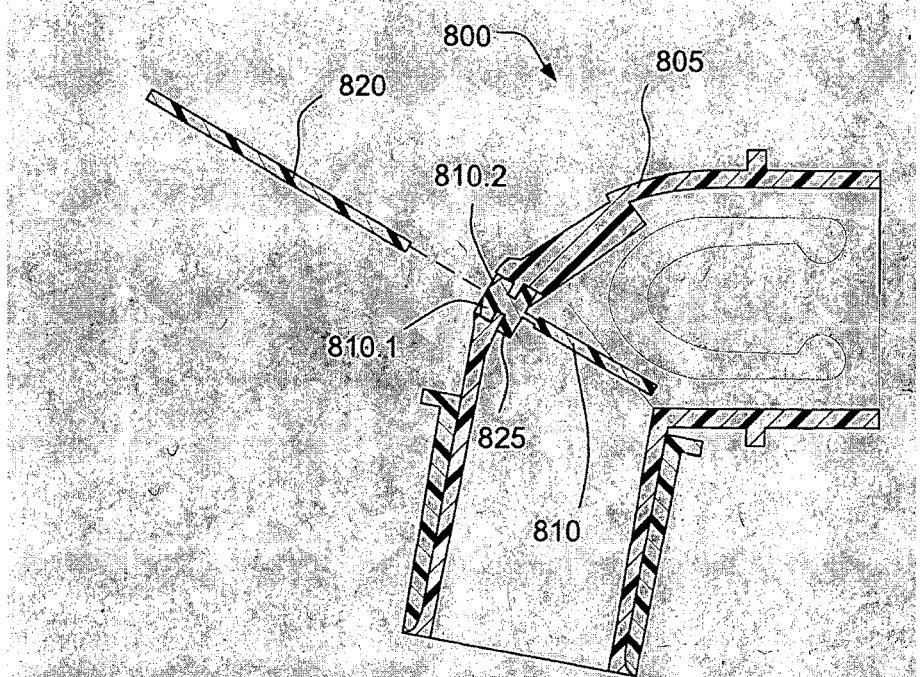

Referring to FIGS. 66 and 67, a tube cuff-to-tube cuff connector 700 assembly may also provide a swivel configured to join cuffs 710, 730 of short tubes with no multiplication of the torque forces. A cuff connector 720 may be provided between two short tubes of, for example, 150 mm in length, rather than one 300 mm tube with 100% clockwise torque force. The cuff connector 720 connects the two short tubes, and each the two short tubes may be wound in different directions, (i.e. 50% clockwise, 50% anti-clockwise) to cancel each other's torque out.

While the technology has been described in connection with what are presently considered to be the most practical and preferred examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., aspects of one example may be combined with aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. An air delivery tube configured to be connected to a patient interface that is configured to deliver positive pressure breathable gas to a patient's airways, the air delivery tube comprising:
 a flexible tubular portion; and
 a connector assembly configured to detachably connect the air delivery tube to the patient interface, the connector assembly comprising:
  a skeleton portion formed from a first material and having a first connection region with a gap, the first connection region being removably connectable to the patient interface and forming a continuous arcuate region, the gap being positioned between opposing ends of an arcuate shape formed by the continuous arcuate region and permitting the first connection region to flex, wherein the gap prevents the continuous arcuate region from forming all of a circular shape, and the continuous arcuate region forms at least a portion of a cylinder; and
  a second component attached to the skeleton portion and formed from a second material.

2. The air delivery tube of claim 1, wherein the first material is relatively more rigid than the second material.

3. The air delivery tube of claim 1, wherein the first material is resilient and/or stiff.

4. The air delivery tube of claim 1, wherein the second material is flexible.

5. The air delivery tube of claim 1, wherein the first material forms a vent.

6. The air delivery tube of claim 1, wherein the second material forms a valve.

7. The air delivery tube of claim 1, wherein the continuous arcuate region includes a stop.

8. The air delivery tube of claim 1, further comprising engagement portions.

9. The air delivery tube of claim 8, wherein the engagement portions are adapted to reduce the size of the gap.

10. The air delivery tube of claim 1, wherein the continuous arcuate region comprises engagement tabs adapted to secure the first connection region of the air delivery tube to the patient interface.

11. The air delivery tube of claim 10, wherein when the continuous arcuate region is flexed, the engagement tabs are in a disengaged position that permits removal of the first connection region of the air delivery tube from the patient interface.

12. The air delivery tube of claim 1, wherein the skeleton portion supports the second component.

13. The air delivery tube of claim 12, wherein the skeleton portion and the second component combine to form a swivel elbow and a valve assembly.

14. The air delivery tube of claim 13, wherein the skeleton portion comprises an underlying structure over which the second component is positioned.

15. The air delivery tube of claim 14, wherein the skeleton portion comprises a first aperture configured to receive the valve assembly and a second aperture configured to receive part of the second component.

16. The air delivery tube of claim 15, wherein the second component comprises a lip defining an aperture configured to receive the valve assembly.

17. The air delivery tube of claim 16, wherein the first aperture of the skeleton portion and the aperture of the second component are aligned.

18. A patient interface system configured to deliver positive pressure breathable gas to a patient's airways, the patient interface system comprising:
 the air delivery tube of claim 1,
 wherein the air delivery tube is configured to be fluidly connected to a patient interface.

19. The patient interface system of claim 18, further comprising the patient interface, the patient interface comprising a cushion configured to sealingly engage the patient's face.

20. The air delivery tube of claim 1, wherein the skeleton portion comprises a second connection region opposite the first connection region, the second connection region being connectable to the flexible tubular portion.

21. An elbow assembly having a first connection region configured to detachably connect to a patient interface, the first connection region comprising:
 a skeleton portion constructed from a first material and including the first connection region, the first connection region having a gap and comprising a continuous circumferential portion that is removably connectable to the patient interface and would form a complete circular shape but for the gap, the continuous circumferential portion forming at least a portion of a cylinder, the gap permitting the first connection region to flex; and
 a second component attached to the skeleton portion and constructed from a second material.

22. The elbow assembly of claim 21, wherein the first material is relatively more rigid than the second material.

23. The elbow assembly of claim 21, wherein the first material is resilient and/or stiff.

24. The elbow assembly of claim 21, wherein the second material is flexible.

25. The elbow assembly of claim 21, wherein the first material forms a vent.

26. The elbow assembly of claim 21, wherein the second material forms a valve.

27. The elbow assembly of claim 21, wherein the continuous circumferential portion includes a stop.

28. The elbow assembly of claim 21, wherein the skeleton portion and the second component are formed in one piece and/or over-molded.

29. The elbow assembly of claim 21, further comprising engagement portions.

30. The elbow assembly of claim 29, wherein the engagement portions are adapted to deform the continuous circumferential portion.

31. The elbow assembly of claim 21, wherein the continuous circumferential portion comprises engagement tabs adapted to secure the first connection region of the elbow assembly to the patient interface.

32. The elbow assembly of claim 31, wherein when the continuous circumferential portion is flexed, the engagement tabs are in a disengaged position that permits removal of the first connection region of the elbow assembly from the patient interface.

33. The elbow assembly of claim 21, wherein the skeleton portion supports the second component.

34. The elbow assembly of claim 33, wherein the skeleton portion and the second component combine to form a swivel elbow and a valve assembly.

35. The elbow assembly of claim 34, wherein the skeleton portion comprises an underlying structure over which the second component is positioned.

36. The elbow assembly of claim 35, wherein the skeleton portion comprises a first aperture configured to receive the valve assembly and a second aperture configured to receive part of the second component.

37. The elbow assembly of claim 36, wherein the second component comprises a lip defining an aperture configured to receive the valve assembly.

38. The elbow assembly of claim 37, wherein the first aperture of the skeleton portion and the aperture of the second component are aligned.

39. A patient interface assembly comprising:
the elbow assembly of claim 21, wherein the elbow assembly is configured to be fluidly connected to the patient interface.

40. The patient interface assembly of claim 39, further comprising the patient interface, the patient interface comprising a cushion configured to sealingly engage a patient's face.

41. The patient interface assembly of claim 40, further comprising an air delivery tube removably attached to the elbow assembly.

* * * * *